(12) United States Patent
Veinot et al.

(10) Patent No.: US 8,410,243 B2
(45) Date of Patent: Apr. 2, 2013

(54) AROMATIC ETHER-CONTAINING FLUORENE MONOMERS, PROCESSES FOR THEIR PREPARATION AND POLYMERIZATION THEREOF

(75) Inventors: Jonathan Gordon Conn Veinot, St. Albert (CA); Leah Coumont, Edmonton (CA); Davin Glenn Piercey, Edmonton (CA); Shaune Lee McFarlane, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 409 days.

(21) Appl. No.: 12/639,402

(22) Filed: Dec. 16, 2009

(65) Prior Publication Data

US 2010/0240856 A1    Sep. 23, 2010

Related U.S. Application Data

(60) Provisional application No. 61/138,370, filed on Dec. 17, 2008.

(51) Int. Cl.
*C08G 65/34* (2006.01)
*C08G 65/38* (2006.01)
*C08G 65/00* (2006.01)

(52) U.S. Cl. ............... 528/425; 528/86; 568/633

(58) Field of Classification Search .............. 528/86, 528/425; 568/633
See application file for complete search history.

(56) References Cited

U.S. PATENT DOCUMENTS 5,900,327 A    5/1999    Pei et al.
6,072,054 A    6/2000    Abd-El-Aziz et al.

FOREIGN PATENT DOCUMENTS

CA    2259721    4/2005

OTHER PUBLICATIONS

Chen et al., "Electrogenerated Chemiluminescence of Polyfluorenes" 89th Canadian Chemistry Conference, Halifax, N.S. (Poster Presentation), May 2008.
McFarlane et al., "Toward Thermally, Oxidatively, and Spectrally Stable Polyfluorene-Based Materials: Aromatic Ether-Functionalized Polyfluorene", Macromolecules, Jan. 6, 2009, pp. 591-598, vol. 42(3), American Chemical Society.
McFarlane et al., "One Pot Synthesis of a Thermally Stable Blue Emitter: Poly[spiro(fluorene-9,9'-(2'-phenoxyxanthene)]", Macromolecules, 2008, 41, pp. 7780-7782.

*Primary Examiner* — Duc Truong
(74) *Attorney, Agent, or Firm* — Bereskin & Parr LLP/S.E.N.C.R.L., s.r.l.; Michael Fenwick

(57) ABSTRACT

Novel aromatic ether-containing monomers are described along with processes for their preparation and their polymerization into corresponding aromatic ether-containing polyfluorenes. These polyfluorenes exhibited stable blue-emission and therefore have application in polymer light-emitting devices.

20 Claims, 8 Drawing Sheets

AROMATIC ETHER-CONTAINING FLUORENE MONOMERS, PROCESSES FOR THEIR PREPARATION AND POLYMERIZATION THEREOF

This application claims the benefit of 35 U.S. §119 based on the priority of U.S. Provisional Application No. 61/138,370, filed Dec. 17, 2008, the contents of which are herein incorporated, in their entirety, by reference.

FIELD OF THE DISCLOSURE

The present disclosure relates to aromatic-ether containing fluorine monomers and polymers derived therefrom. The present disclosure further relates to uses of the novel aromatic-ether containing polyfluorenes as materials for photoluminescence and electroluminescence in light emitting devices.

BACKGROUND OF THE DISCLOSURE

Blue-emitting polyfluorene (PF) polymers are being pursued as active materials in polymer light-emitting diodes,[1] lasers,[2-6] and sensors.[7-12] To meet the requirements of practical device application, high-molecular-weight blue-emitting poly(p-phenylene) (PPP) materials including, ladder-type PPPs,[13] polyfluorenes (PF),[14] polyindenofluorenes (PIFs),[15] and polytetrahydrophenanthrene (PTHP)[16] have being widely investigated. Alkyl-substituted PFs, such as poly(9,9'-dioctylfluorene) (PFO), are among the most promising candidates for optoelectronic applications.[17] Still, the inherent spectral instability of alkyl-substituted PFs (i.e. green emission upon exposure to thermal stressing) remains a significant challenge limiting full realization of their device potential.

It is now well-established that the primary source of the undesirable green emission is fluoreneone defects formed during and/or after polymer synthesis.[18] Attempts to prevent defect formation have included derivitization at the 9-position with trifluoromethyl,[19] silole,[20] siloxane,[21] silsesquioxane,[22] polyphenylene,[23] and dendritic benzyl-ether[24] moieties. These studies clearly show that controlling the molecular structure of PF at the 9-position affords one solution toward improving material performance.

Poly(aryl ethers) (PAEs) are well known engineering thermoplastics possessing excellent thermal, chemical, radiation, and oxidative stability.[25, 26] Jiang et al. prepared a series of PAE polymers bearing pendent alkyl-substituted oligofluorenes.[27, 28]

Two classical methods for preparing aromatic ethers (AEs) are the copper-mediated Ullmann-ether synthesis[29, 30] and electron-withdrawing-group (EWG)-facilitated nucleophilic-aromatic-substitution ($S_NAr$) protocols.[25, 31] These approaches are generally ineffective in preparing high purity materials for organic electronics (e.g., PLEDs) because elevated temperatures, copper salts, and EWGs are required for the reaction to go to completion and are difficult to remove from the product. In addition, it is difficult to prepare materials in a controlled stepwise fashion, thereby limiting control over subtle changes in molecular structure. Fine structural control is well known to dramatically impact material properties.

SUMMARY OF THE DISCLOSURE

Two unique fluorene monomers (PTE I(a) and MTE (Ib)) and polyfluorene-based homopolymers (PPTE III(a) and PMTE III(b)) containing covalently linked aromatic-ether (AE) moieties were synthesized via microwave Ni(0)-mediated Yamamoto coupling reactions. The monomers and polymers demonstrated thermal stabilities, as determined by TGA, much higher than that of the status quo poly(9,9'-dioctylfluorene) (PFO) (i.e. greater than 100° C.), and most importantly, the spectral emission remained stable after annealing in ambient and inert atmospheres. PPTE and PMTE were annealed in an $N_2$ atmosphere at 200° C. for 72 hours and at 150 ° C. in ambient atmosphere for 1 hour showing no evidence of green emission, in stark contrast to PFO. The results show that PFs with AE moieties present in the 9-position exhibit stable blue-emission with potential application in polymer light-emitting diodes (PLEDs).

Accordingly, the present disclosure includes novel aromatic ether-containing fluorene monomers of the Formula I:

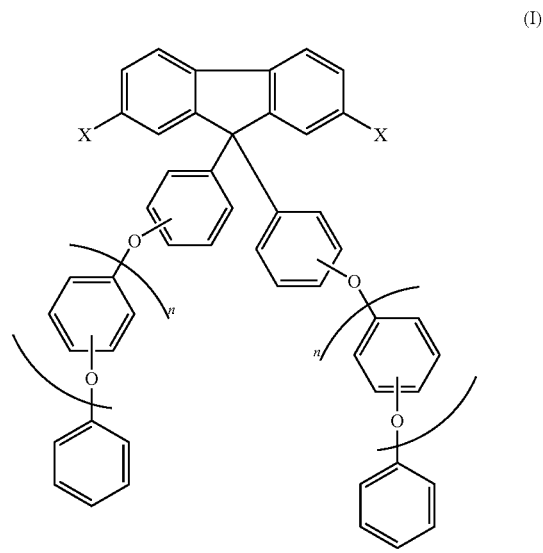

(I)

wherein X is a polymerization-enabling leaving group; and n is 0 or 1.

There is also included in the present disclosure a process for the preparation of compounds of Formula I:

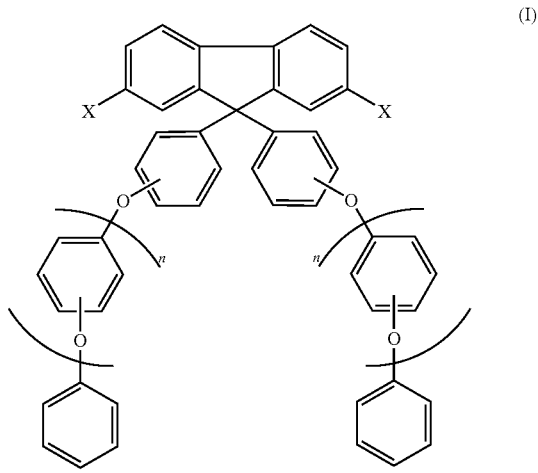

(I)

wherein X is a polymerization-enabling leaving group; and n is 0 or 1, comprising:
(a) reacting a compound of the Formula IV:

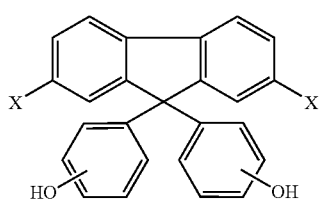

wherein X is a polymerization-enabling leaving group, with a compound of the Formula V:

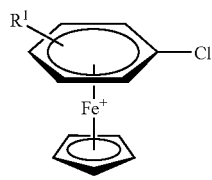

wherein $R^1$=H for compounds of Formula I wherein n is 0 and $R^1$=Cl for compounds of Formula I wherein n is 1, under conditions to form a compound of the Formula VI:

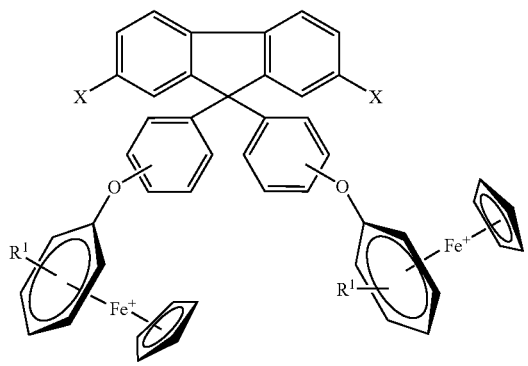

wherein X is a polymerization-enabling leaving group and $R^1$ is H for compounds of Formula I wherein n is 0 and $R^1$ is Cl for compounds of Formula I wherein n is 1;
(b) when $R^1$ is H, reacting the compounds of Formula VI under conditions to remove the CpFe⁺ group to form a compound of Formula I wherein n is 0; or
when $R^1$ is Cl, reacting the compounds of the Formula VI with a compound of the Formula VII:

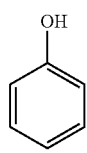

under conditions to form a compound of the Formula VIII:

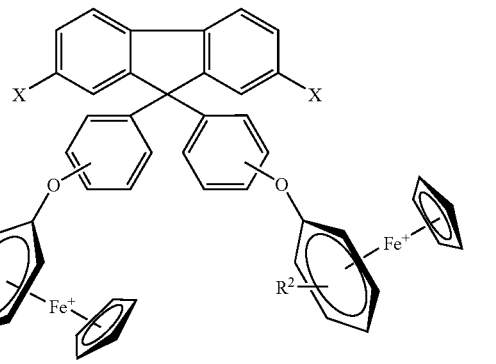

wherein $R^2$ is O-Ph; and
(c) treating the compounds of the Formula VIII under conditions to remove the CpFe⁺ group to form a compound of Formula I wherein n is 1.

In a further embodiment of the present disclosure, there is included an aromatic-ether-containing polyfluorene comprising repeating monomeric units of the Formula II:

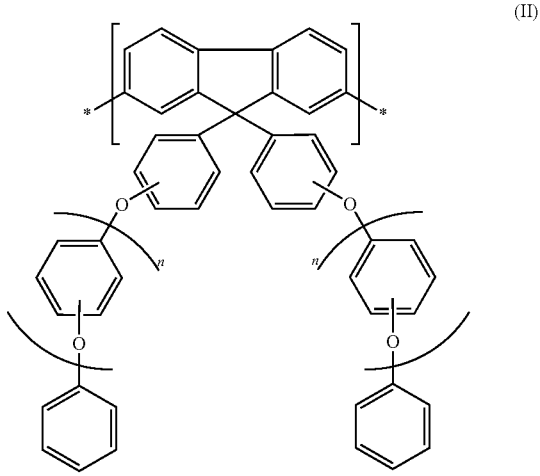

wherein n is 0 or 1.

It another embodiment of the present disclosure, there is included an aromatic-ether-containing polyfluorene of the Formula III:

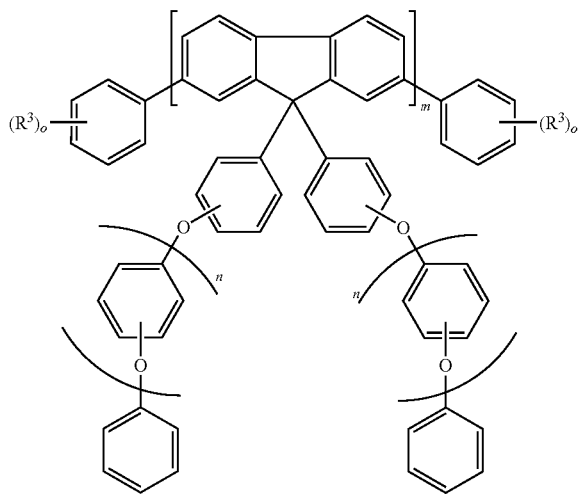

(III)

wherein $R^3$ is $C_{1-6}$alkyl;
m is an integer from 1 to 10,000;
n is 0 or 1; and
o is 0, 1, 2, 3, 4 or 5.

In yet another embodiment of the present disclosure, there is included a light-emitting solid state device comprising an aromatic-ether containing polyfluorene of the present disclosure.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in greater detail with reference to the following drawings in which.

Figure 1:
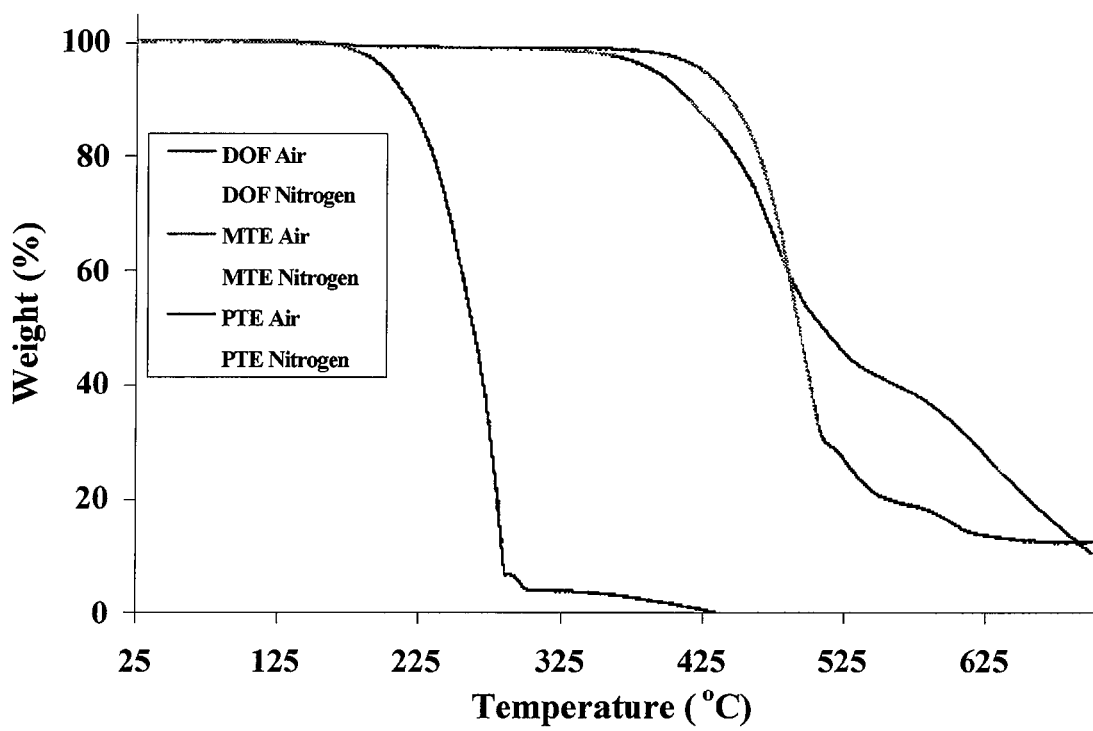
FIG. 1 shows TGA curves of DOF, MTE I(a) and PTE I(b) monomers in an air and $N_2$ atmosphere at a heating rate of 10° C./min.

DETAILED DESCRIPTION OF THE DISCLOSURE (I) Definitions

The term "$C_{1-6}$alkyl" as used herein refers to straight or branched chain alkyl groups containing from 1, 2, 3, 4, 5 or 6 carbon atoms and includes, for example, methyl, ethyl, n-propyl, isopropyl, n-butyl, isobutyl, t-butyl, n-pentyl, n-hexyl, isopentyl, and the like.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Monomers of the Disclosure

The present disclosure includes novel aromatic ether-containing fluorene monomers of the Formula I:

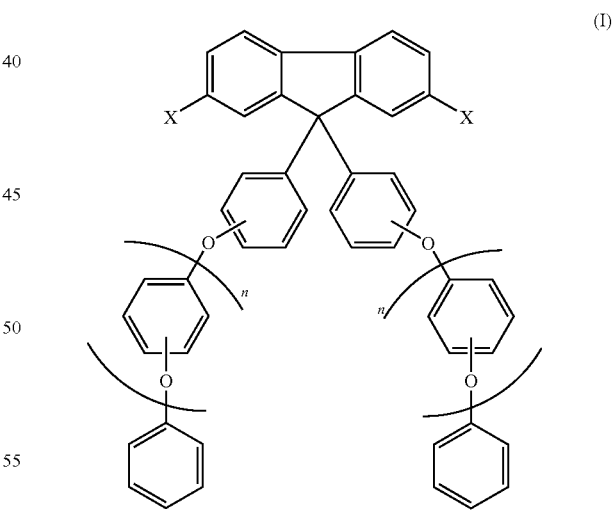

(I)

wherein X is a polymerization-enabling leaving group; and
n is 0 or 1.

In an embodiment of the disclosure, X is bromo. In a further embodiment of the disclosure, n is 1. In another embodiment of the disclosure, the aromatic ethers are attached at positions that are meta or para to each other.

In yet another embodiment, the monomer of Formula I has the following structure:

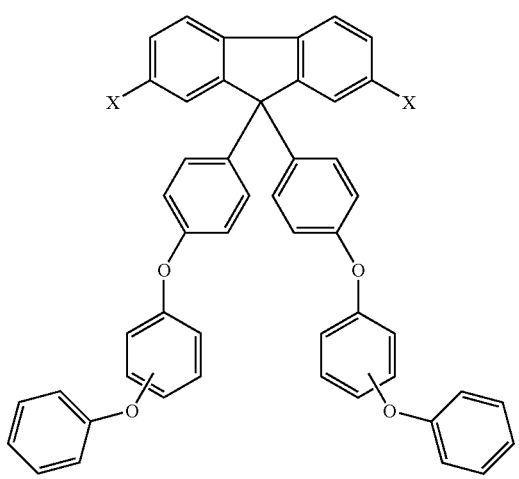

wherein X is a polymerization-enabling leaving group, for example bromo.

In another embodiment, the monomers of Formula I are selected from:

I(a)

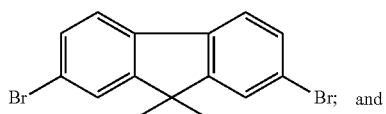

I(b)

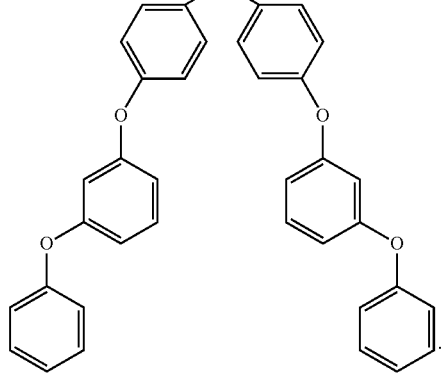

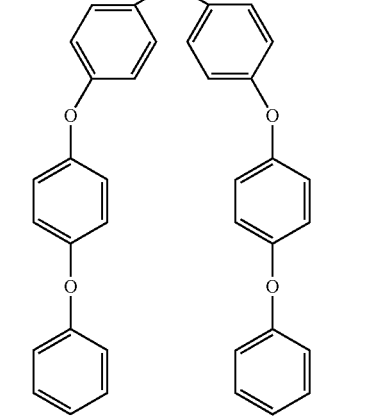 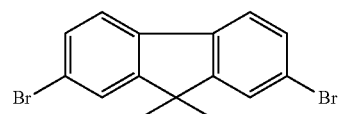

in $N_2$ and air occurs at substantially higher temperatures (ca. 150° C.) than that for DOF. This increased stability is attributed to the stabilizing influence of the AE moieties. It is also noted that the onset of decomposition of I(a) and I(b) is approximately the same in both $N_2$ and air, in stark contrast to DOF. While note wishing to be limited by theory, this may indicate the lack of a readily accessible decomposition pathway for AE-containing I(a) and I(b).

The present disclosure also describes $S_NAr$ protocols utilizing transition-metal-mediated activation of aromatic rings as a method for preparing AE bonds in AE containing fluorene monomers. In particular, the process for preparing monomers of Formula I comprise iron-based methodologies utilizing cyclopentadienyliron (CpFe$^+$) as an activating group,[32] which is readily removed, leaving behind wholly AE containing material.

Accordingly, there is included in the present disclosure a process for the preparation of compounds of Formula I:

(I)

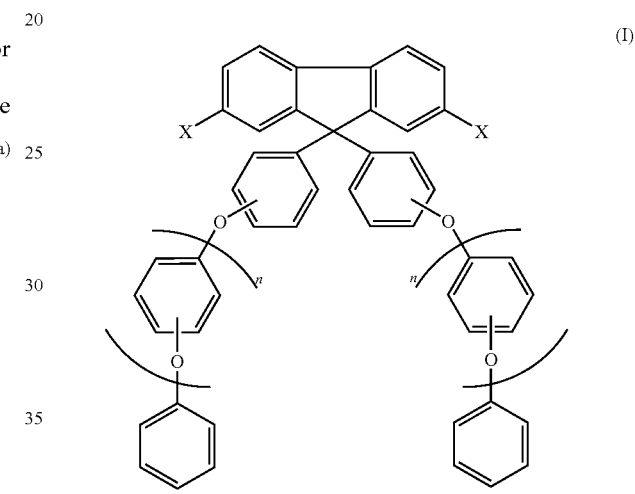

wherein X is a polymerization-enabling leaving group; and n is 0 or 1,
comprising:
(a) reacting a compound of the Formula IV:

(IV)

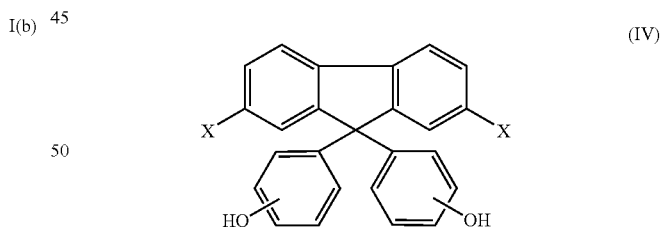

wherein X is a polymerization-enabling leaving group, with a compound of the Formula V:

(V)

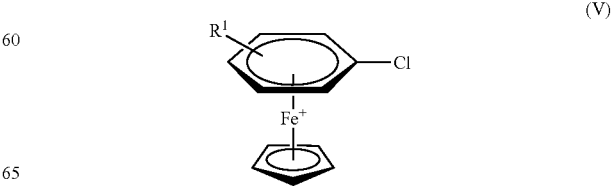

Table 1 summarizes and FIG. 1 shows that the onset of decomposition (10% weight loss) of I(a) (PTE) and I(b) MTE wherein R¹=H for compounds of Formula I wherein n is 0 and R¹=Cl for compounds of Formula I wherein n is 1, under conditions to form a compound of the Formula VI

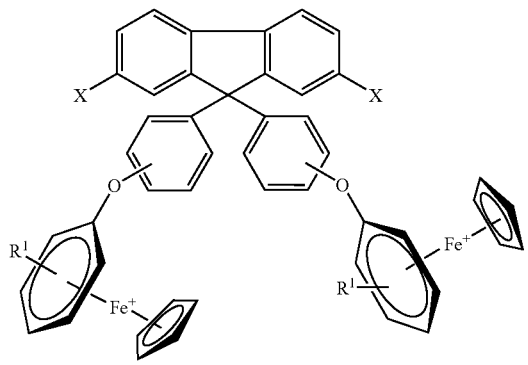

(VI)

wherein X is a polymerization-enabling leaving group and R¹ is H for compounds of Formula I wherein n is 0 and R¹ is Cl for compounds of Formula I wherein n is 1;

(b) when R¹ is H, reacting the compounds of Formula VI under conditions to remove the CpFe⁺ group to form a compound of Formula I wherein n is 0; or when R¹ is Cl, reacting the compounds of the Formula VI with a compound of the Formula VII:

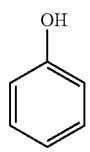

(VII)

under conditions to form a compound of the Formula VIII:

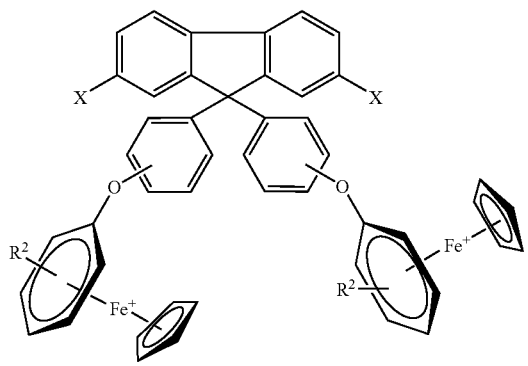

(VIII)

wherein R² is O-Ph; and
(c) treating the compounds of the Formula VIII under conditions to remove the CpFe⁺ group to form a compound of Formula I wherein n is 1.

In an embodiment of the disclosure, the conditions to form a compound of the Formula VI comprise reacting the compounds of Formula IV and V in the presence of a base in an inert solvent, such as dimethylformamide (DMF) at room temperature for about 12 hours to about 36 hours, suitably about 24 hours. In an embodiment, the base is $K_2CO_3$ In a further embodiment of the present disclosure, the conditions to remove the CpFe⁺ group comprise reacting the compound of Formula VI or VIII in a suitable high boiling solvent and heating, suitably in a microwave reactor, to a temperature of about 150° C. to about 250° C., suitably about 200° C., for about 10 to about 15 minutes, suitably about 12 minutes.

In another embodiment of the present disclosure the conditions to form a compound of the Formula VIII comprise reacting the compounds of the Formula VI and VII presence of a base in an inert solvent, such as dimethylformamide (DMF) at room temperature for about 48 to about 96 hours, suitably about 72 hours. In an embodiment, the base is $K_2CO_3$.

It is a further embodiment of the present disclosure, that in the preparation of the compounds of the Formula VIII, the compounds of the Formula VI, wherein R¹ is Cl are not isolated. In this embodiment, once the formation of the compounds of the Formula VI wherein R¹ is Cl is complete, the compound of the Formula VII and base are added directly to the reaction mixture and the reaction allowed to continue to provide the compounds of the Formula VIII.

(III) Polymers of the Disclosure

Polymerization of the AE-containing fluorene monomers of the present disclosure, utilizing microwave initiated Yamamoto-coupling,[37] yielded blue-emitting AE-functionalized PFs. Thermogravimetric analysis (TGA) and thermal-oxidative degradation studies at ambient temperature confirm that the incorporation of AE units at the 9-position substantially improves the thermal, oxidative, and color stability of these new materials when compared to status quo alkyl-functionalized PFs (i.e. PFO). The inclusion of AE structural units provides a straightforward approach towards eliminating adverse affects of thermal degradation of PF materials.

Accordingly, the present disclosure includes an aromatic-ether-containing polyfluorene comprising repeating monomeric units of the Formula II:

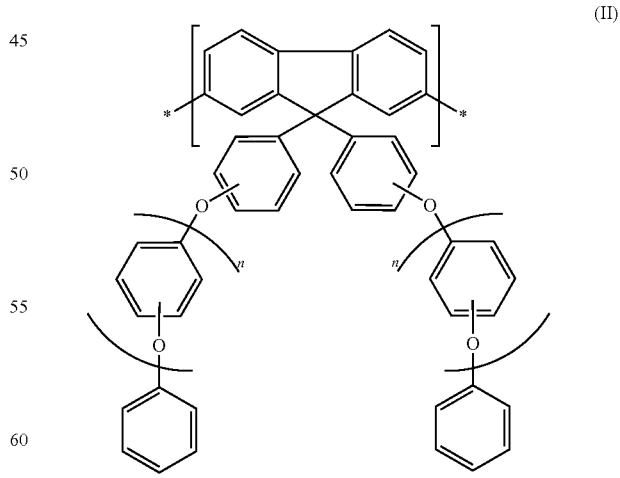

(II)

wherein n is 0 or 1.

In an embodiment of the present disclosure the aromatic-ether-containing polyfluorene comprises repeating monomeric units selected from II(a)

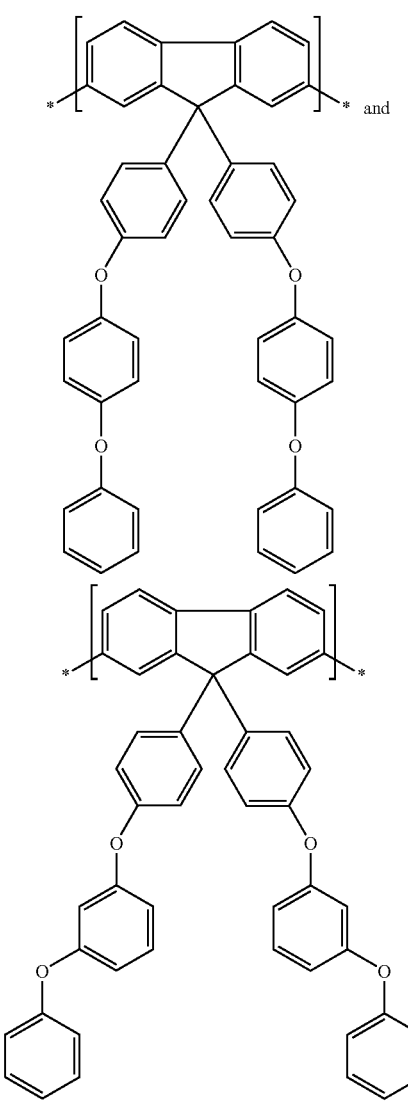

II(b)

It another embodiment of the present disclosure, there is included an aromatic-ether-containing polyfluorene of the Formula III:

(III)

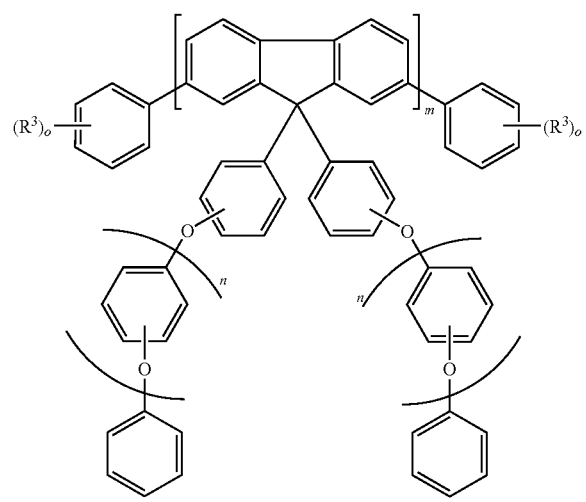

wherein $R^3$ is $C_{1-6}$alkyl;
m is an integer from 1 to 10,000;
n is 0 or 1; and
o is 0, 1, 2, 3, 4 or 5.

In an embodiment of the disclosure, n is 1. In a further embodiment of the disclosure $R^3$ is methyl or ethyl, suitably methyl and o is 1, 2 or 3, suitably 2. In a further embodiment of the disclosure, o is 2 and the 2 $R^3$ groups are located at the 3 and 5 positions of the phenyl ring.

The value of m varies as desired to achieve desired properties such as solubility, proccessability, formability and the like as would be known to a person skilled in the art.

In a further embodiment of the disclosure, the aromatic-ether-containing polyfluorene of the Formula III is selected from:

III(a)

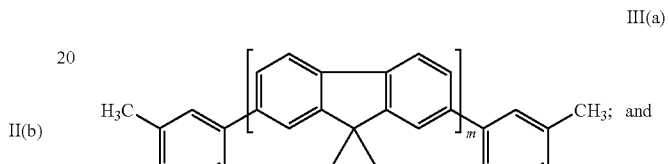

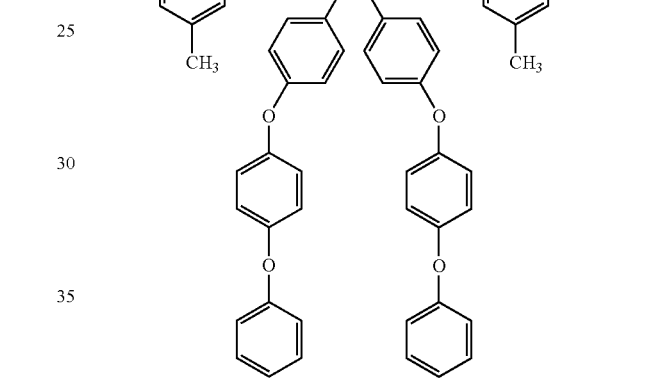

III(b)

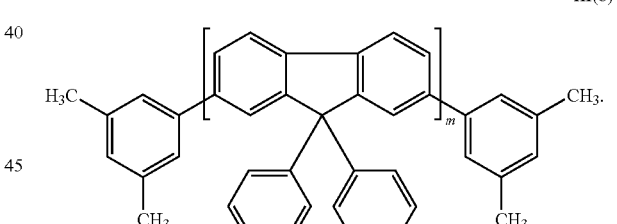

The polymers of Formula III are prepared using Yamamoto-coupling initiated in a microwave reactor. It is appreciated that any suitable end-capping agent can be used in the polymerization reaction. Such agents are known to those skilled in the art.

In an embodiment of the disclosure the AE-containing polyfluorenes are homopolymers. In a further embodiment the AE-containing polyfluorenes are copolymerized with other monomers. Usually copolymerization is used to reduce the cost of materials by reducing the fluorene content. Representative comonomeric materials include olefin units such as ethylene, propylene and the like, aromatic units such as styrene and the like and ester units. If comonomeric units are present, the leaving groups X, are selected to accommodate the additional comonomers in the polymerization. The relative weight proportion of the comonomeric units will range from 100:0 (for pure polyfluorene homopolymer) to about 10:90 for a highly diluted material.

Compounds III(a) (PPTE) and III(b) (PMTE), shown above, exhibit significantly higher thermal decomposition temperatures than PFO, indicating AE moieties substantially improve the thermal and oxidative stability of PFs.

Figure 8:
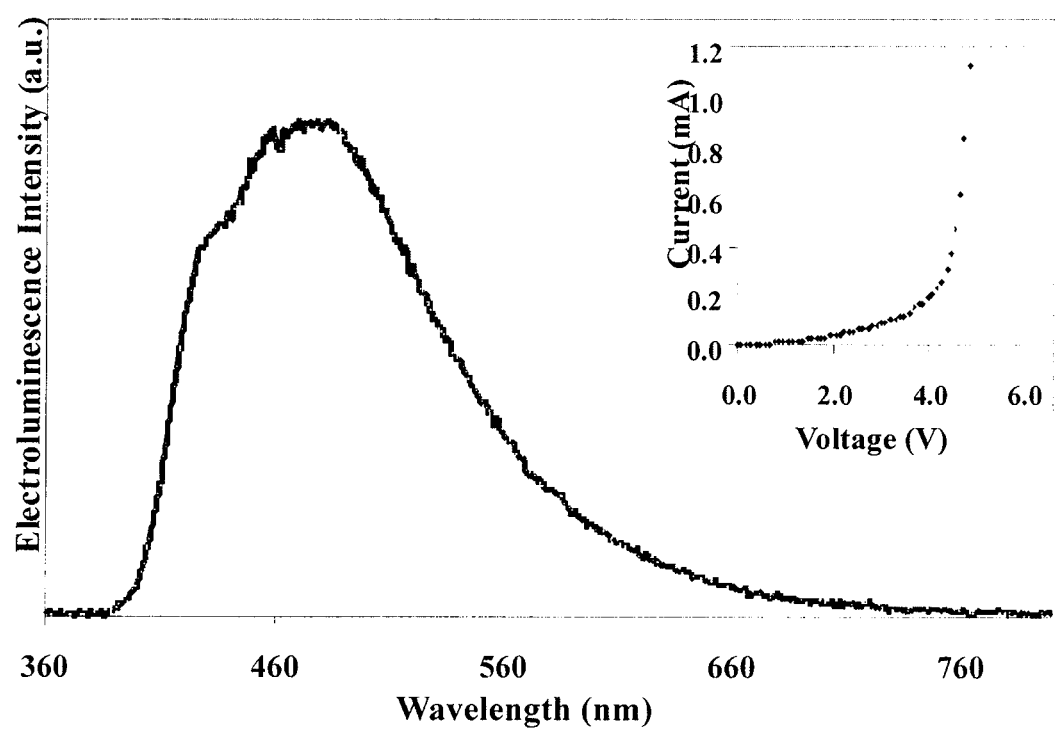
FIG. 8 shows an electroluminescence spectrum and Current-Voltage (I-V) (inset) characteristics of a PLED fabricated with PMTE III(b) as the emitting layer.

Thermal annealing of PPTE, PMTE, and PFO in air show very different affects on the PL spectra. PFO shows a dramatic increase in green emission (ca. 550 nm) after annealing in air for 60 minutes at 150° C. and the resulting green emission visibly dominates film color after only 20 minutes of thermal stressing.[45] In contrast, the PL spectra of PPTE and PMTE exhibit negligible change under identical conditions which severely degrade PFO Proof-of-concept polymer light-emitting diodes (PLEDs) with PMTE III(b) as the emitting layer were fabricated with the following sandwich structure: ITO/PEDOT-PSS/PMTE/Ca/Al (ITO=indium tin oxide; PEDOT-PSS=polyethylenedioxythiophene polystyrene sulfonate). The electroluminescence spectrum acquired in ambient conditions did not shift over device testing time (ca. 30 min). PMTE exhibited turn-on voltages of ca. 4.5 V and exhibited blue electroluminescence as shown in FIG. 8.

Accordingly, in yet another embodiment of the present disclosure, there is included a light-emitting solid state device comprising an aromatic-ether containing polyfluorene of the present disclosure, i.e. an an aromatic-ether-containing polyfluorene comprising repeating monomeric units of the Formula II or an aromatic-ether-containing polyfluorene of the Formula III. In an embodiment, the light-emitting solid state device is configured as a light-emitting diode or a light-emitting electrochemical cell.

The following non-limiting examples are illustrative of the present disclosure:

EXAMPLES

General Information:

All reagents and solvents were purchased from commercial sources and used without further purification unless specified. Potassium carbonate was purchased from Mallinckrodt; concentrated HCl was purchased from EMD; dimethylformamide (DMF), acetic anhydride, toluene, >99% phenol, 98% ferrocene, 99% aluminum chloride, 99.99% ammonium hexafluorophosphate, 99.9% Chromium(VI) oxide, 99+% 1,4-dichlorobenzene, 98% 1,3-dichlorobenzene, anhydrous 99% 1,5-cyclooctadiene (cod), >99% 2,2'-bipyridyl (bpy) dried on a Schlenk line for 16 hrs and 97% 5-bromo-m-xylene were purchased from Aldrich; diethylether, methanol, acetone, ethyl acetate, hexane, and 2,7-dibromofluorene (1) were purchased from Alfa Aesar; 98% Ni(cod)$_2$ and 99.7% aluminum powder were purchased from Strem; 2,7-dibromofluorene-9-one (2) and 2,7-dibromo-9,9'-bis(4-hydroxyphenyl)-9H-fluorene (3) were prepared according to a literature procedures[39] as shown in Scheme 1.

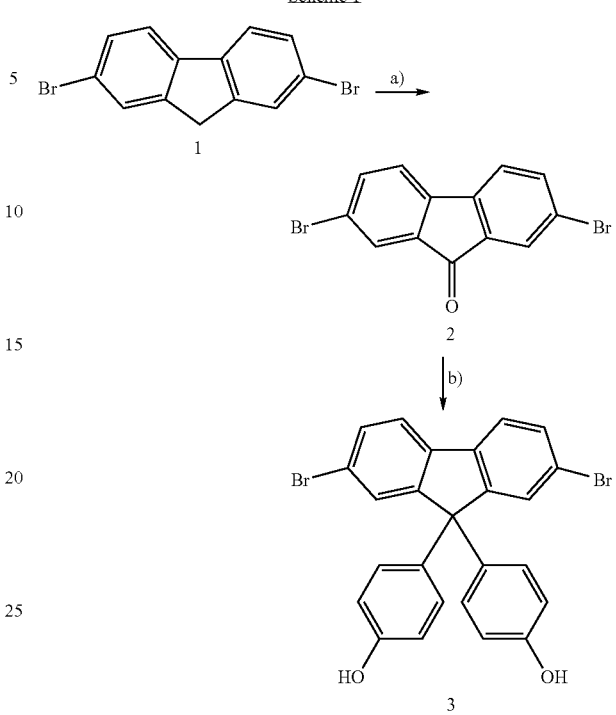

(a) CrO$_3$, ethyl acetate, stir for 24 hrs; (b) phenol, methanesulfonic acid, 3-mercaptopropionic acid, 70° C. for 20 hrs. $\eta^6$-1,4-dichlorobenzene-$\eta^5$-cyclopentadienyliron-hexafluorophosphate (4a) and $\eta^6$-1,3-dichlorobenzene-$\eta^5$-cyclopentadienylironhexafluorophosphate (4b) were prepared according to literature procedures.[41] (5b) was not isolated. Microwave syntheses were carried out with a Biotage Initiator system. $^1$H-NMR and $^{13}$C-NMR spectra were recorded with a Varian Inova 400 (400 MHz and 100 MHz, respectively) and Varian 500 (500 MHz and 125 MHz, respectively) spectrometers. Elemental analysis was performed with a Carlo Erba CHNS-O EA1108 elemental analyzer. Photoluminescence (PL) and excitation spectra were obtained with a Varian Cary Eclipse Fluorescence Spectrophotometer. UV-vis spectra were obtained with an Agilent 8453 UV-vis spectrophotometer. Low resolution mass spectrometry was performed with an Applied Biosystems Voyager Elite matrix-assisted laser desorption time-of-flight (MALDI-TOF) system and high resolution mass spectrometry was performed with a Bruker 9.4T Fourier-transform ion-cyclotron resonance (FTICR) and an Applied Biosystems Mariner orthogonal acceleration time-of-flight (ao-TOF) systems. Thermogravimetric analysis (TGA) was performed on a Perkin Elmer Pyris 1 system at a heating rate of 10° C./min. Differential scanning calorimetry (DSC) was performed with a TA Instruments Q1000 system at various heating and cooling rates. GPC analysis was performed on an Agilent 1100 series system equipped with a Waters Styragel® HR 4E column.

PLED Fabrication/Electroluminescence Testing:

Indium-tin-oxide (ITO) coated glass substrates (8-12 Ω/sq., Delta Tech.) were sonicated in IPA, dried at 120° C., and exposed to an O$_2$ plasma for one minute. Hole injection PEDOT/PSS (Aldrich) was applied from a 2.8% w/v aqueous solution and heated at 60° C. for 10 minutes in a class 10 cleanroom. Active layers were prepared from 0.5% w/v toluene solutions and heated at 70° C. for 15 minutes in an N₂ filled glovebox. Electrical contacts were fabricated by sequentially depositing ca. 5 nm of Ca and ca. 150 nm of Al. PLED electroluminescence spectra were obtained in air using a Varian Cary Eclipse fluorescence spectrophotometer. IV curves were collected using a computer-controlled Keithley 2400 source.

Example 1

Monomer Experimental

The monomers of the disclosure were prepared in as shown in Scheme 2. Details of these syntheses are provided below.

(a) PIBC (5a)

2,7-dibromo-9,9'-bis(4-hydroxyphenyl)-9H-fluorene (3) (4.98 g, 9.72 mmol), $\eta^6$-1,4-dichlorobenzene-$\eta^5$-cyclopentadienylironhexafluorophosphate ((4a) 8.03 g, 19.44 mmol) and potassium carbonate (2.69 g, 19.44 mmol) along with 100 mL of DMF were combined in a 250 mL round bottom flask. The dark brown solution was covered with aluminum foil and stirred under an argon atmosphere at 50° C. for 24 hours. The resulting purple solution was poured into 1200 mL of a 10% HCl (aq) solution yielding a yellow precipitate. Ammonium hexafluorophosphate (3.17 g, 19.44 mmol) was dissolved in distilled water and added to the yellow precipitate to ensure complete precipitation. The yellow precipitate was collected over a Buchner funnel and washed with copious amounts of

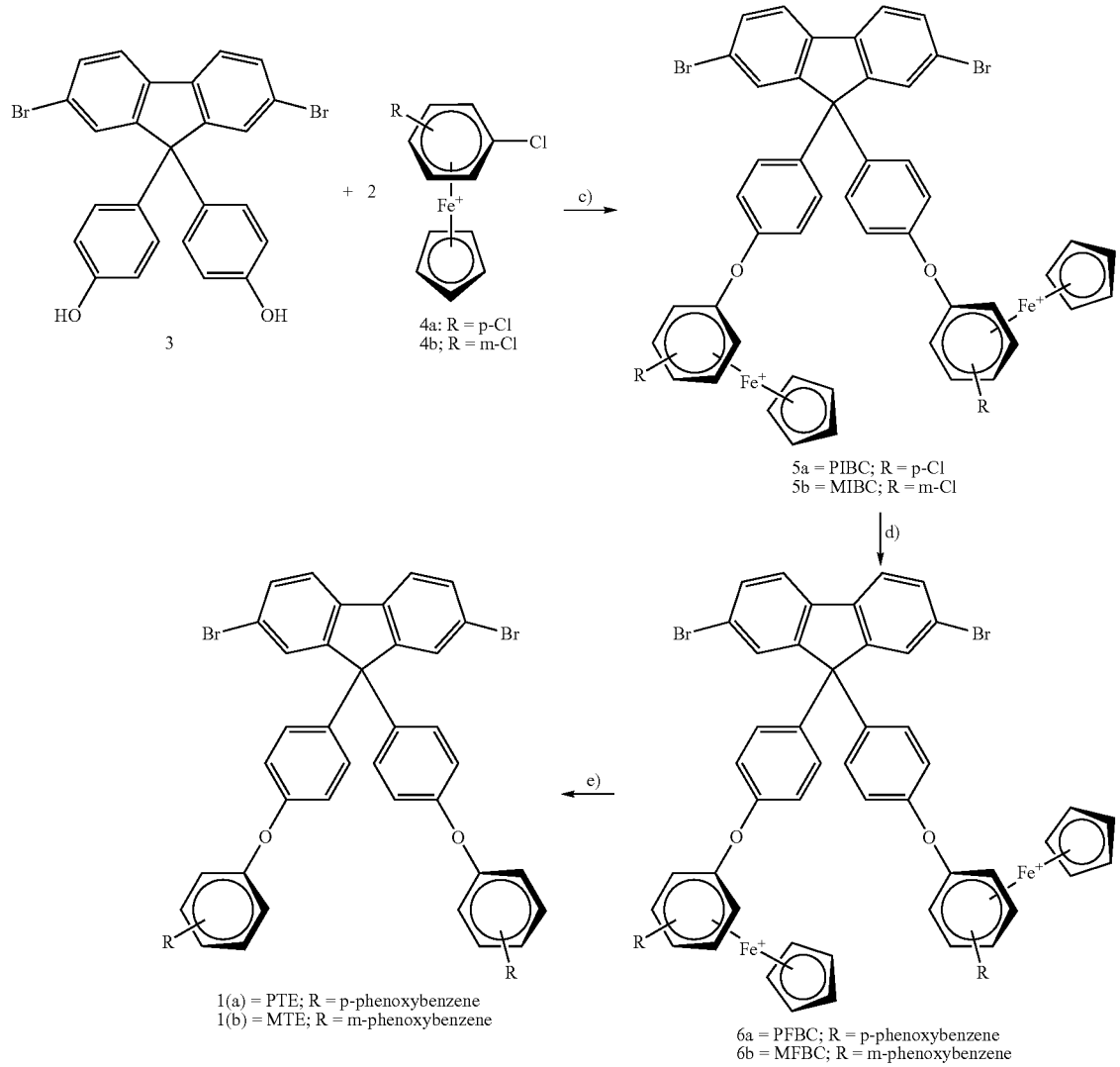

Scheme 2

5a = PIBC; R = p-Cl
5b = MIBC; R = m-Cl

1(a) = PTE; R = p-phenoxybenzene
1(b) = MTE; R = m-phenoxybenzene

6a = PFBC; R = p-phenoxybenzene
6b = MFBC; R = m-phenoxybenzene (c) K₂CO₃, dissolve 3 and 4a or 4b in DMF, stir at room temperature for 24 hours, isolation of 5a and 5b is not necessary prior to proceeding to the next synthetic step;
(d) K₂CO₃, phenol, more DMF, stir at room temperature for 72 hours; (e) dissolve 6a and 6b in DMF and CH₃CN, dimethylglyoxime and heat for 12 minutes at 200° C. in a microwave reactor.

distilled water. When completely dry, the powder was washed a further 3 times with a total of 200 mL of diethyl ether giving a pale yellow powder (10.12 g, 83%). ¹H-NMR (400 MHz, d₆-DMSO): δ 8.00 (d, J=8.0 Hz, 2 H); 7.68 (m, J=8.0 Hz, 4 H); 7.28 (m, J=8.8 Hz, 8 H); 6.79 (d, J=6.4 Hz, 4 H); 6.43 (d, J=6.4 Hz, 4 H); 5.25 (s, 10 H). ¹³C-NMR (100 MHz, d₆-DMSO): δ 152.21, 152.07, 141.78, 137.72, 131.49, 131.44, 129.84, 128.65, 123.10, 121.51, 120.54, 103.59, 86.74, 79.31, 76.51, 64.23. HRMS Calculated for $C_{47}H_{32}O_2Br_2Fe_2$ [$M^{2+}=M-2PF_6$]: 967.88339. Found: 967.88202. Elemental Analysis for $C_{47}H_{32}O_2Cl_2Br_2Fe_2P_2F_{12}$: C, 44.76; H, 2.56. Found: C, 45.67; H, 2.95.

(b) PFBC (6a)

2,7-dibromo-9,9'-bis(4-hydroxyphenyl)fluorene (3) (2.00 g, 3.94 mmol), $\eta^6$-1,4-dichlorobenzene-$\eta^5$-cyclopentadienylironhexafluorophosphate (4a) (3.30 g, 7.99 mmol) and potassium carbonate (1.6 g, 11.6 mmol) along with 80 mL of DMF were combined in a 500 mL round bottom flask. The green/brown solution was covered with aluminum foil and stirred under an argon atmosphere at room temperature for 24 hours. Potassium carbonate (1.6 g, 11.6 mmol) and phenol (0.80 g, 8.5 mmol) along with an additional 40 mL of DMF was added to the solution and allowed to stir for an additional 72 hours. The resultant brown solution was poured into 800 mL of a 10% HCl (aq) solution forming a yellow precipitate. The yellow solid was collected over a Buchner funnel and washed with copious amounts of distilled water. When completely dry the solid was washed with ~600 mL of diethyl ether giving a yellow powder (5.35 g, 99%). $^1$H-NMR (500 MHz, $d_6$-DMSO): δ 7.99 (d, J=8.1 Hz, 2 H); 7.68-7.48 (m, 8 H); 7.40-7.14 (m, 14 H); 6.28 (m, 8 H); 5.20 (s, 10 H). $^{13}$C-NMR (125 MHz, $d_6$-DMSO): δ 153.30, 152.85, 151.11, 141.39, 137.69, 131.41, 130.67, 130.13, 129.74, 129.45, 128.61, 126.19, 123.11, 121.47, 120.36, 120.23, 77.86, 75.47, 74.96, 64.17. Elemental Analysis for $C_{59}H_{42}O_4Br_2Fe_2P_2F_{12}$: C, 51.49; H, 3.08. Found: C, 50.20; H, 3.18.

(c) MFBC (6b)

2,7-dibromo-9,9'-bis(4-hydroxyphenyl)-9H-fluorene (3) (1.03 g, 2.03 mmol), $\eta^6$-1,3-dichlorobenzene-$\eta^5$-cyclopentadienylironhexafluorophosphate (4b) (1.65 g, 4.00 mmol) and potassium carbonate (0.80 g, 5.79 mmol) along with 40 mL of DMF were combined in a 100 mL round bottom flask. The dark brown solution was covered with aluminum foil and stirred under an argon atmosphere at room temperature for 24 hours. Potassium carbonate (0.8 g, 5.79 mmol) and phenol (0.4 g, 4.24 mmol) along with an additional 20 mL of DMF was added to the brown/black solution and allowed to stir for an additional 72 hours. The resulting dark-orange solution was poured into 400 mL of a 10% HCl (aq) solution producing an orange/beige precipitate. After stirring for a few minutes the precipitate was collected over a Buchner funnel and washed with copious amounts of distilled water. When completely dry, the powder was washed a further 3 times with a total of 200 mL of diethyl ether giving a fine off-white powder (2.68 g, 99%). $^1$H-NMR (500 MHz, $d_6$-DMSO): δ 8.01 (d, J=8.0 Hz, 2H); 7.95 (s, 2 H); 7.72-7.50 (m, 8 H); 7.40-7.25 (m, 12 H); 6.41 (s, 2 H); 6.34 (t, J=6.1 Hz, 2 H); 6.20 (d, J=5.4 Hz, 2 H); 6.11 (d, J=5.6 Hz, 2 H); 5.20 (s, 10 H). $^{13}$C-NMR (125 MHz, $d_6$-DMSO): δ 153.06, 152.69, 152.22, 141.61, 137.80, 132.22, 131.56, 131.53, 130.77, 129.83, 128.69, 126.43, 123.23, 121.59, 120.68, 120.44, 84.36, 77.69, 74.14, 73.72, 68.01, 64.27. HRMS Calculated for $C_{59}H_{42}O_4Br_2Fe_2$ [$M^{2+}=M-2PF_6$]: 1084.01376. Found: 1084.01300. Elemental Analysis for $C_{59}H_{42}O_4Br_2Fe_2P_2F_{12}$: C, 51.49; H, 3.08. Found: C, 49.75; H, 3.30.

(d) PTE (I(a))

2,7-dibromo-9,9'-bis[4-($\eta^6$-1,4-diphenoxy-$\eta^5$-cyclopentadienyliron hexafluorophosphate)benzene] (PFBC-6a) (1.00 g, 0.73 mmol) was added to each of five 20 mL microwave vials followed by 10 mL of DMF, 10 mL of acetonitrile, 0.92 g of dimethylglyoxime and a stirbar yielding a brown solution. The vial was capped and placed in a microwave reactor for 12 minutes at 200° C. The resulting opaque black-solutions were poured into 600 mL of a 10% HCl (aq) solution and stirred for 5 hours before being filtered over a Buchner funnel yielding a brown filtrate and black residue. The black residue was dried before being suspended in 75 mL of toluene and filtered through celite. The celite was washed with an additional 75 mL of toluene giving a pale yellow filtrate that after evaporation yielded a yellow solid. The solid was dissolved in a minimal amount of dichloromethane and added drop-wise to 500 mL of 90% ethanol resulting in a white precipitate. The combined white solids were filtered over a Buchner funnel and washed twice with a total of 1000 mL of 100% ethanol (1.06 g, 34%). The solid was further purified with silica-gel column chromatography using a 10:1 hexane/ethyl acetate mixture as mobile phase. $^1$H-NMR (500 MHz, CDCl$_3$): δ 7.59 (d, J=9.0 Hz, 2 H); 7.49 (m, J=1.5 Hz, 4 H); 7.33 (m, J=7.5, 1.0 Hz, 4 H); 7.10 (m, J=9.0, 2.0 Hz, 6 H); 6.99 (m, J=2.0 Hz, 12 H); 6.87 (m, J=9.0, 2.5 Hz, 4 H). $^{13}$C-NMR (125 MHz, CDCl$_3$): δ 157.71, 157.29, 153.26, 153.08, 152.06, 138.60, 137.96, 131.06, 129.78, 129.31, 123.12, 121.95, 121.70, 121.02, 120.49, 118.39, 117.78, 64.54. HRMS Calculated for $C_{49}H_{32}Br_2O_4$: 842.06618. Found: 842.06619. Elemental Analysis for $C_{49}H_{32}Br_2O_4$: C, 69.68; H, 3.82. Found: C, 69.15; H, 3.82.

(e) MTE (I(b))

2,7-dibromo-9,9'-bis[4-($\eta^6$-1,3-diphenoxy-$\eta^5$-cyclopentadienyliron hexafluorophosphate)benzene] (MFBC-6b) (1.00 g, 0.73 mmol) was added to a 30 mL microwave vial followed by 10 mL of DMF, 10 mL of acetonitrile, 0.92 g of dimethylglyoxime and a stirbar yielding an orange/red solution. The vial was capped and placed in a microwave reactor for 12 minutes at 200° C. The resulting opaque black-solution was poured into 120 mL of a 10% HCl (aq) solution and stirred for 5 hours before being filtered over a Buchner funnel yielding a red/brown filtrate and black residue. The black residue was dried before being suspended in 15 mL of toluene and filtered through celite. The celite was washed with an additional 15 mL of toluene giving a light-orange filtrate that after evaporation yielded a light-orange solid. The solid was dissolved in a minimal amount of dichloromethane and added dropwise to 100 mL of 90% ethanol resulting in a white precipitate. 10 mL of distilled water was then added to the 100 mL of 90% ethanol to help coagulate any remaining material. The combined white solids were filtered over a Buchner funnel and washed twice with a total of 200 mL of 100% ethanol (0.40 g, 60%). The solid was further purified with silica-gel column chromatography using a 7:1 hexane/ethyl acetate mixture as mobile phase. $^1$H-NMR (400 MHz, CDCl$_3$): δ 7.59 (dd, J=7.6, 0.8.Hz, 2 H); 7.49 (dd, J=7.6, 2 Hz, 2 H); 7.48 (s, 2 H); 7.33 (t, J=7.6 Hz, 4 H); 7.25 (t, J=8.0 Hz, 2 H); 7.10 (d, J=8.8 Hz, 4 H); 7.10 (t, J=7.6 Hz, 2H); 7.02 (d, J=7.6 Hz, 4 H); 6.90 (d, J=8.4 Hz, 4 H); 6.73 (m, J=7.8 Hz, 4 H); 6.68 (t, J=2.4 Hz, 2 H). $^{13}$C-NMR (100 MHz, CDCl$_3$): δ 158.63, 157.97, 156.50, 156.05, 152.99, 139.13, 137.86, 131.01, 130.36, 129.74, 129.27, 129.21, 123.62, 121.89, 121.63, 119.20, 118.65, 118.57, 113.55, 113.44, 109.58, 64.58. HRMS Calculated for $C_{49}H_{32}Br_2O_4$: 842.06618. Found: 842.06619. Elemental Analysis for $C_{49}H_{32}Br_2O_4$: C, 69.68; H, 3.82. Found: C, 69.41; H, 3.86.

Example 2

Polymer Experimental

The monomers of the disclosure were prepared in as shown in Scheme 3. Details of these syntheses are provided below.

Scheme 3

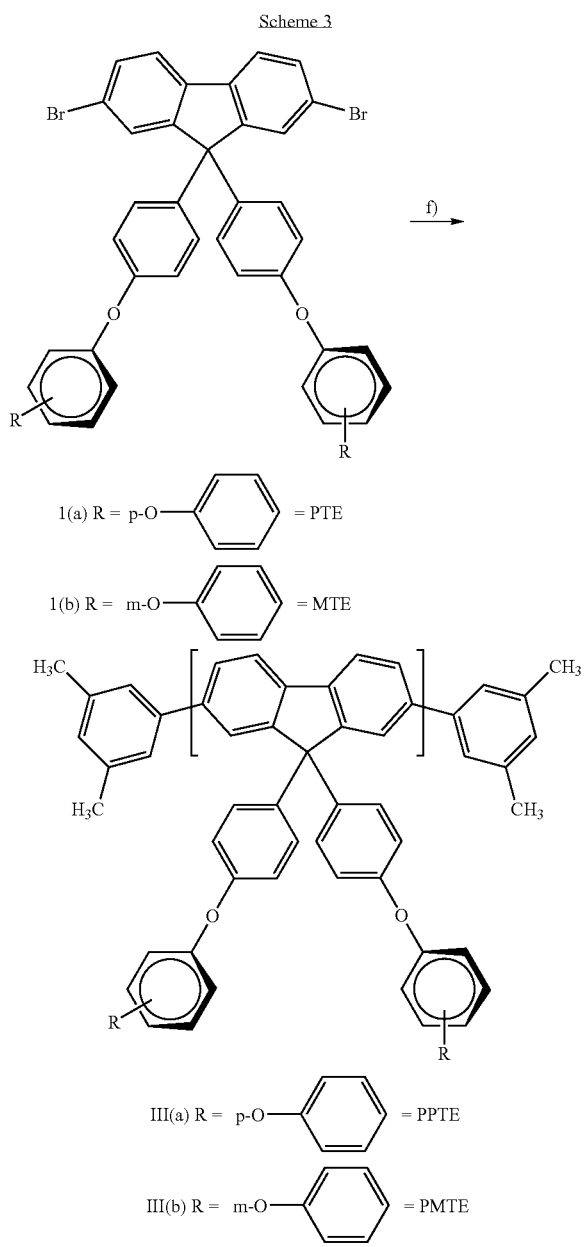

(f) Combine I(a) or I(b), DMF/toluene~1:2, Ni(cod)₂, 2,2'-bipyridyl, 1,5-cyclooctadiene, 5-bromo-m-xylene in a microwave vial and heat for 10 minutes at 230° C.

(a) PPTE (III(a))

PTE I(a) (0.200 g, 0.237 mmol) was placed in a Biotage 10-20 mL microwave vial along with byp (0.098 g, 0.632 mmol), Ni(cod)₂ (0.168 g, 0.611 mmol), and 1,5-cyclooctadiene (0.08 mL, 0.7 mmol) inside an argon filled glove-box forming a purple paste. The mixture was diluted in 9 mL of DMF and 14 mL toluene, followed by 5-bromo-m-xylene (1.6 μL, 0.0118 mmol) as an end-capping agent resulting in a red solution. The vial was capped and irradiated in a Biotage Initiator microwave system for 10 minutes at an internal temperature of 230° C. The purple/black contents of the vial were poured into 150 mL of methanol and the polymer was allowed to agglomerate overnight. The blue/grey slurry was transferred to the thimble of a soxhlet extractor and washed with 300 mL of acetone for 24 hours followed by an extraction with 300 mL toluene for 24 hours. The toluene was removed by rotary evaporator yielding a green flaky solid (0.160 g, 98%). The solid was subsequently dried in a vacuum oven at ~100° C. for 24 hours. ¹H-NMR and ¹³C-NMR spectra were acquired after filtering a toluene-d8 solution through a 0.2 um Millipore Millex-GN filter. ¹H-NMR (500 MHz, toluene-d₈): δ 7.9-7.8 (m, 2H) 7.7-7.5 (m, 6 H); 7.4-7.1 (m, 7 H); 6.9-6.4 (m, 33 H). ¹³C-NMR (125 MHz, toluene-d₈): δ 158.27, 157.65, 157.50, 153.46, 153.39, 153.27, 152.94, 152.66, 152.49, 141.61, 140.61, 140.46, 140.05, 139.51, 129.96, 129.82, 129.28, 129.16, 128.47, 128.23, 125.61, 123.17, 121.34, 121.20, 120.74, 118.68, 117.98, 65.22. MALDI-TOF mass spectrometry polymer repeat unit (C₄₉H₃₂O₄): Calculated; 684.776. Found; ~685 a.m.u. Elemental Analysis calculated for C₄₉H₃₂O₄ polymer repeat unit: C, 85.94; H, 4.71. Found: C, 80.64; H, 5.37. Also found 0.42% nitrogen.

(b) PMTE (III(b))

MTE I(b) (0.150 g, 0.178 mmol) was placed in a Biotage 10-20 mL microwave vial along with bpy (0.074 g, 0.474 mmol), Ni(COD)₂ (0.126 g, 0.458 mmol), and 1,5-cyclooctadiene (0.06 mL, 0.5 mmol) inside an argon filled glove-box forming a purple paste. The mixture was diluted in 6.8 mL of DMF and 10.5 mL toluene, followed by 5-bromo-m-xylene (1.2 μL, 0.00885 mmol) as an end-capping agent, forming a brown solution. The vial was capped and irradiated in a Biotage Initiator microwave system for 10 minutes at an internal temperature of 230° C. The purple/green contents of the vial were poured over a 1:1:1 solution of acetone:methanol:HCl (conc) forming a cloudy white solution and brown oil. The polymer was extracted with 4×100 mL portions of toluene resulting in an orange organic layer that was subsequently dried over magnesium sulphate. Following gravity filtration the toluene was removed by rotary evaporator yielding a brown flaky solid (0.111 g, 89%). The solid was subsequently dried in a vacuum oven at ~100° C. for 24 hours. ¹H NMR and ¹³C-NMR spectra were acquired after filtering a CDCl₃ solution through a 0.2 um Millipore Millex-GN filter. ¹H-NMR (400 MHz, CDCl₃): δ 7.92-7.70 (m, 2H) 7.68-7.45 (m, 4 H); 7.44-7.26 (m, 4 H); 7.24-7.03 (m, 8 H); 7.02-6.94 (m, 4 H); 6.92-6.80 (m, 4 H); 6.76-6.56 (m, 6 H). ¹³C-NMR (100 MHz, CDCl₃): δ 158.68, 158.43, 158.17, 156.55, 155.86, 155.70, 141.00, 130.30, 129.75, 129.73, 129.45, 129.36, 129.24, 126.94, 126.05, 124.60, 123.57, 119.20, 119.18, 118.58, 113.45, 113.32, 113.26, 113.22, 109.55, 109.45, 64.6. MALDI-TOF mass spectrometry polymer repeat unit (C₄₉H₃₂O₄): Calculated; 684.776. Found; ~685 a.m.u. Elemental Analysis calculated for C₄₉H₃₂O₄ polymer repeat unit: C, 85.94; H, 4.71. Found: C, 75.09; H, 5.80. Also found 2.03% nitrogen.

Results and Discussion for Examples 1 and 2

Monomer Synthesis

Intermediate compound 2,7-Dibromofluoren-9-one[38] (2) and target precursor compound 2,7-Dibromo-9,9'-di-(4-hydroxyphenyl)-9H-fluorene[39] (3), as shown in Scheme 1, were prepared according to literature procedures and characterized with ¹H and ¹³C NMR spectroscopy, and electron-impact (EI) mass spectrometry. The crystal structure of (3) was reported previously.[40]

(3) was subsequently reacted with 4a or 4b,[41] as outlined in Scheme 2, to generate p-intermediate-bimetallic-complex (PIBC) 5a or m-intermediate-bimetallic-complex (MIBC) 5b. Isolation of PIBC or MIBC was not necessary; both were further reacted with additional phenol to produce p-final-bimetallic-complex (PFBC) 6a or m-final-bimetallic-complex (MFBC) 6b, respectively. The CpFe+ moieties on the bimetallic complexes PFBC and MFBC were removed via microwave irradiation to generate p-tetra-ether (PTE) I(a) and m-tetra-ether (MTE) I(b), respectively. Compounds 5-7a,b were characterized with $^1$H- and $^{13}$C-NMR spectroscopy, high-resolution mass spectrometry (HRMS), and elemental analysis (EA).

Thermal and Oxidative Stability of PTE and MTE Monomers

TGA of PTE (I(a)), MTE (I(b)), and purified 2,7-dibromo-dioctylfluorene (DOF), in $N_2$ and air, provided insight into the thermal and oxidative stability of AE functionalized monomers as well as direct comparison with DOF. Table 1 summarizes and FIG. 1 shows the onset of decomposition (10% weight loss) of MTE and PTE in $N_2$ and air occurs at substantially higher temperatures (ca. 150° C.) than for DOF. This increased stability is attributed to the stabilizing influence of the AE moieties. It is also noted that the onset of decomposition of PTE and MTE is approximately the same in both $N_2$ and air, in stark contrast to DOF. This may indicate the lack of a readily accessible decomposition pathway for AE-containing PTE and MTE.

Thermal Phase Behavior of PTE and MTE Monomers

Differential scanning calorimetry (DSC) provides insight into the phase behavior of PTE (I(a)) and MTE (I(b)) monomers. Table 1 summarizes the melting temperatures ($T_m$), purity, and glass transition temperatures ($T_g$) of PTE and MTE as determined by DSC. PTE and MTE exhibit well-defined melting temperatures ($T_m$) of 166 and 181° C., respectively, when heated from 35 to 250° C. on the first heating cycle. Upon cooling (10° C./min) and reheating (10° C./min) the sample, the well-defined melting temperatures are replaced by PTE and MTE glass transition temperatures of 78 and 53° C., respectively. The appearance of PTE and MTE glass transitions indicate that the cooling rate employed (10° C./min) during the DSC run was faster than nucleation and subsequent crystal growth. Similar behavior has been noted for glass forming, high $T_g$, bulky spiro compounds in which the crystallization kinetics are slowed.[42] Importantly, the higher $T_g$'s exhibited by PTE and MTE are expected to translate into AE-based polymers with higher $T_g$'s than PFO,[43] and increased emission stability.

Synthesis of PPTE III(a) and PMTE III(b) Polymers

The role of microwave technology in organic synthesis is expanding greatly and is now beginning to be utilized in organic polymer syntheses. One of the primary advantages of this synthetic technique is significantly decreased reaction times that make high throughput material synthesis viable. Highlighting this point, the first report of a PF-type polymer synthesis using microwave irradiation appeared in 2002.[44] Carter outlined the successful polymerization of alkyl-substituted PF materials in 10 minutes; a dramatic advancement over the traditional 3-4 days required for conventional thermal heating. A microwave-based approach was employed for the polymerization of the AE-functionalized PTE and MTE monomers of the present disclosure, and poly-p-tetra-ether (PPTE) III(a) and poly-m-tetra-ether (PMTE) III(b), as shown in Scheme 3. PPTE and PMTE were characterized with $^1$H- and $^{13}$C-NMR spectroscopy, gel permeation chromatography (GPC), MALDI-TOF mass spectrometry and elemental analysis (EA).

Thermal Phase Behavior of PPTE III(a) and PMTE III(b) Polymers

Figure 2:
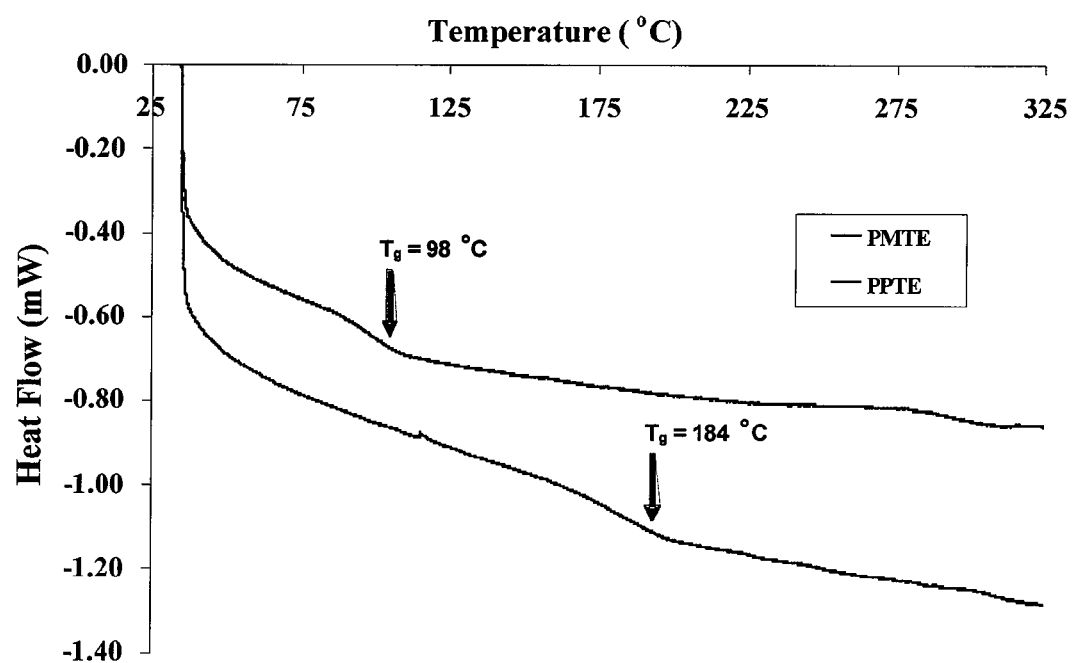
FIG. 2 shows DSC traces of PPTE III(a) (red) and PMTE III(b) (blue) at a heating rate of 10° C./min. The samples were dried for 24 hours at ca. 100° C. in a vacuum oven prior to analysis.

The glass transition temperature ($T_g$) of PPTE III(a) and PMTE III(b) were evaluated with DSC at a heating rate of 10° C./min as shown in FIG. 2 and Table 2. The glass transition temperature of PPTE (184° C.) is substantially higher than PMTE (98° C.), which is attributed to PPTEs higher molecular weight and more symmetric side chains.

Thermal Stability Characterization of PPTE III(a) and PMTE III(b) Polymers

Figure 3:
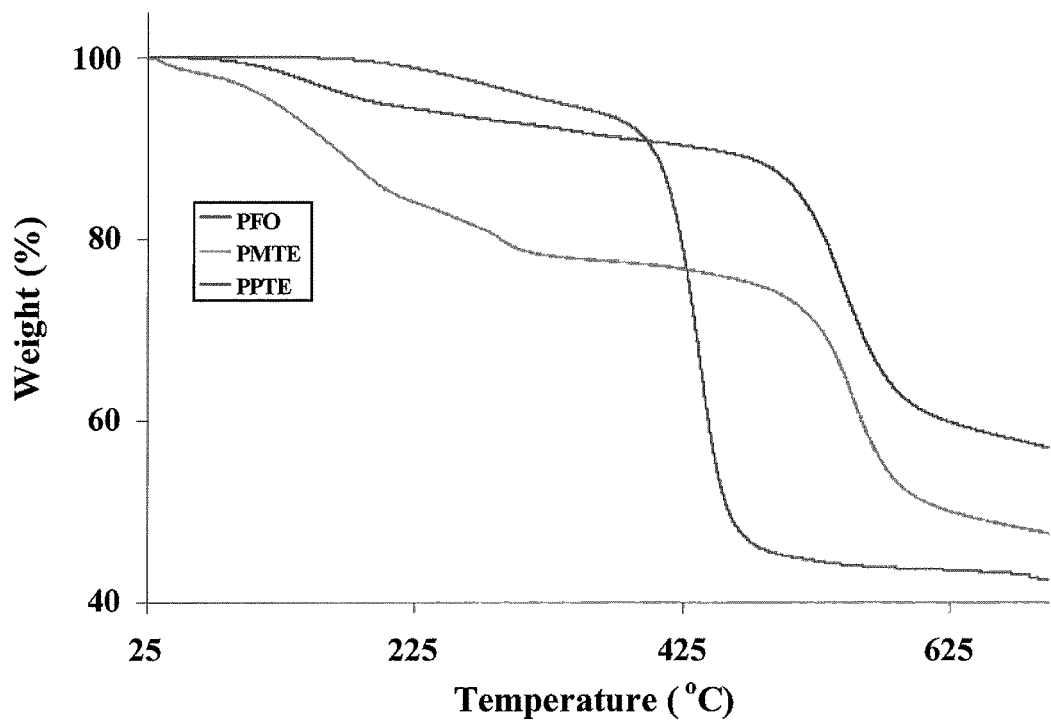
FIG. 3 shows TGA traces of PFO (green), PMTE III(a) (red) and PPTE (IIIb) (blue) in a $N_2$ atmosphere at a heating rate of 10° C./min after being dried for 24 hours in vacuum at ca. 100° C. The traces correspond to a single TGA heating run.

TGA investigations of PPTE III(a), PMTE III(b), and commercially available PFO, in $N_2$ and air atmospheres, were conducted to gain direct comparison of their thermal and oxidative stability. FIG. 3 and Table 2 show PPTE and PMTE lose approximately 10 and 20% of their weight prior to plateauing at ca. 320° C. These polymers subsequently undergo another weight loss, which is attributed to decomposition of the polymer, at 528 and 515° C. respectively. If PPTE and PMTE are first heated to 320° C., cooled to 25° C., and reheated to 700° C., similar decomposition temperatures (534 and 515° C.) are observed (See FIG. 4). While the weight loss up to 320° C. could be attributed to the liberation of volatile impurities (e.g., solvent) remaining following synthesis and workup, placing PPTE and PMTE in a vacuum oven at ca. 100° C. for 24 hours did not address this issue. Elemental analysis of PPTE and PMTE revealed carbon content to be ca. 5% and 10% below theoretically predicted values and nitrogen contamination of ca. 0.5 and 2.0%, respectively was noted.

Figure 4:
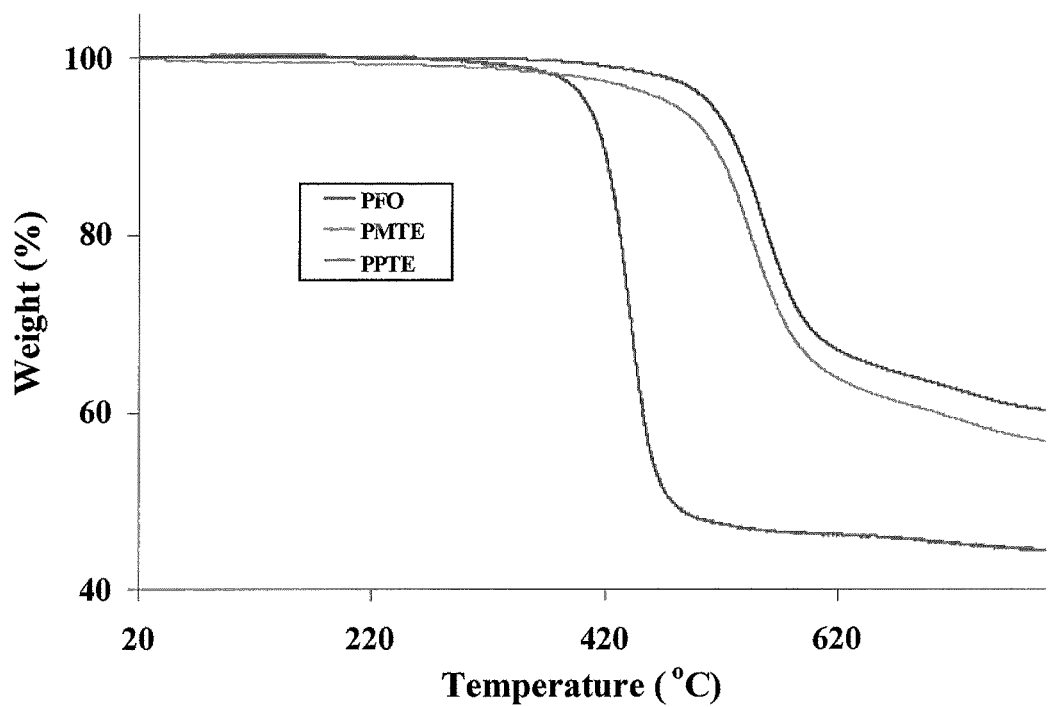
FIG. 4 shows TGA traces of PFO (green), PMTE III(a) (red) and PPTE III(b) (blue) in a $N_2$ atmosphere at a heating rate of 10° C./min. The traces correspond to material that has been pre-treated by heating the sample in a TGA crucible from 25 to 320° C., cooling it back down to 25° C. and heating the sample again to 700° C.

PPTE II(a) and PMTE II(b), shown in FIG. 4, exhibit significantly higher thermal decomposition temperatures than PFO, indicating AE moieties substantially improve the thermal and oxidative stability of PFs. The improvement in thermal stability of the AE-containing polymers (PPTE and PMTE) of the present disclosure over PFO is smaller (ca. 100° C.) than the difference in stability between the AE-containing monomers and DOF (ca. 150° C.), indicating that monomer stability does not necessarily quantitatively correlate with polymer stability.

Photoluminescence Stability of PPTE III(a) and PMTE III(b) Polymers

Figure 5:
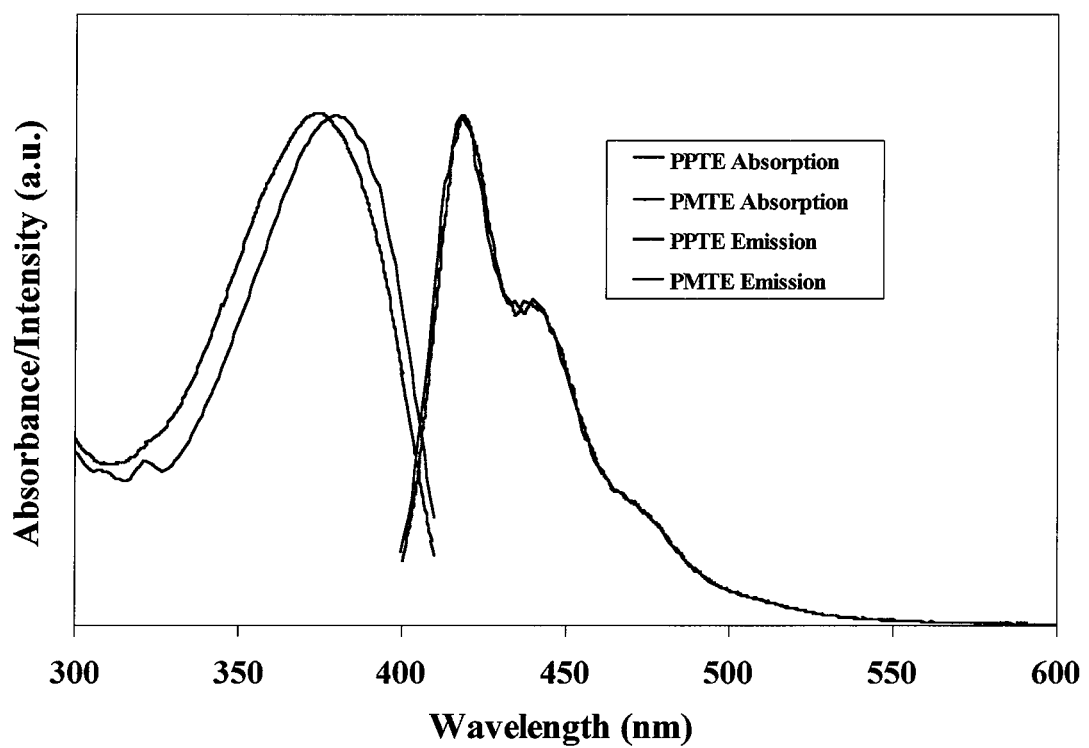
FIG. 5 shows UV-vis and PL spectra ($\lambda_{ex}$=350 nm) of a 0.001% w/v and a 0.00001% w/v toluene solution of PPTE III(a) (blue) and PMTE II(b) (red).
Figure 6:
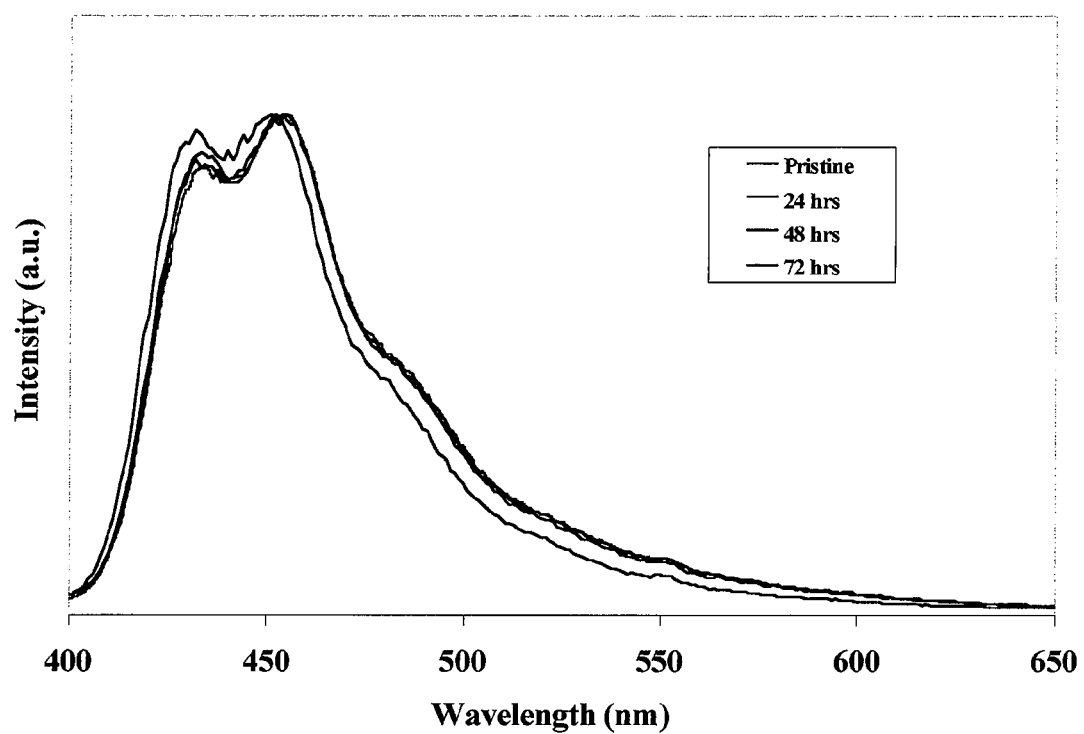
FIG. 6 shows PL spectra ($\lambda_{ex}$=350 nm) of a drop-coated PPTE III(a) film annealed at 200° C. for indicated times in an $N_2$ filled glove-box.

FIG. 5 and Table 2 show solution UV-vis and photoluminescence (PL) spectra of PPTE III(a) and PMTE III(b). These spectra are consistent with polymer formation and similar to those obtained for alkyl-substituted PF materials (e.g. PFO). Films of PPTE, PMTE, and PFO drop-coated and/or spin-coated from 1% w/v toluene solutions onto quartz substrates were evaluated for thermal and morphological stability upon thermal annealing in an $N_2$ atmosphere. In an effort to ensure removal of excess toluene, films were dried in ambient prior to drying in vacuo (ca. 30 mTorr) for 24 hours. Upon annealing a PFO film at 200° C., in an inert $N_2$ atmosphere, the PL spectrum continuously evolved over 80 hours resulting in three changes to the spectrum: (1) the contribution to the spectrum from each of the vibronic components change; (2) a shift in the relative positions of these transitions; (3) the intensity of the PL, in the green spectral region (ca. 550 nm), increases.[45] These changes are well established and have been attributed to polymer chain reordering and excimer formation.[46] In contrast to commercial PFO, PPTE and PMTE display spectral stability when annealed under identical conditions, as shown in FIG. 6.

Figure 7:
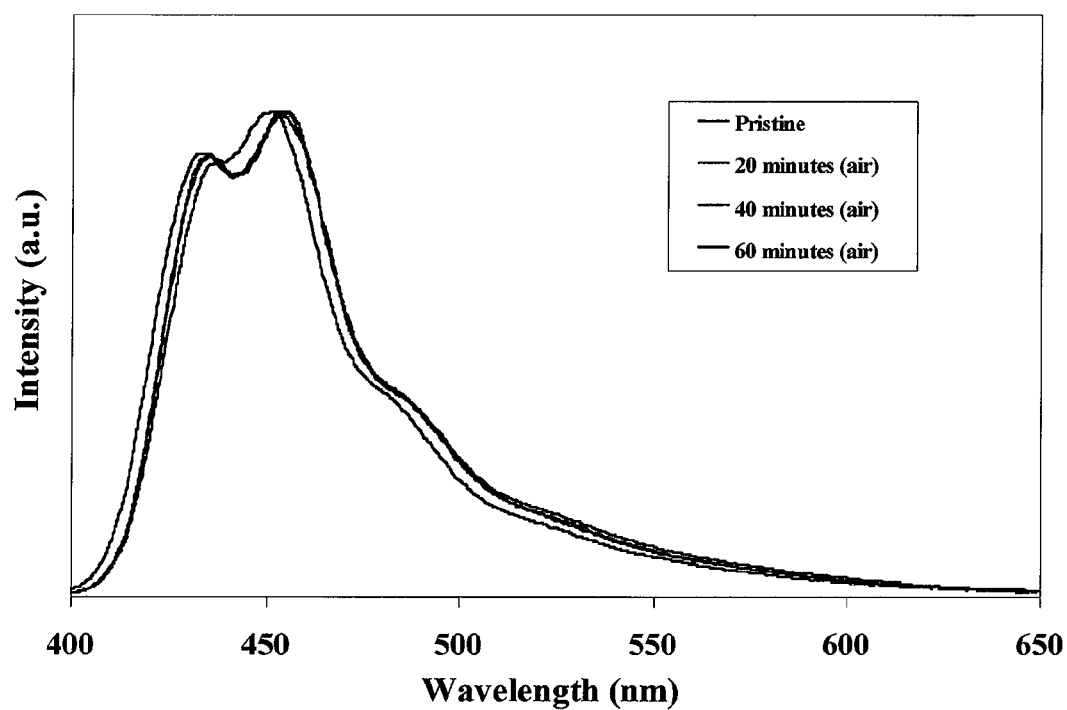
FIG. 7 shows PL spectra ($\lambda_{ex}$=350 nm) of a drop-coated PPTE III(a) film annealed at 150° C. for indicated times under ambient conditions.

Thermal annealing of PPTE, PMTE, and PFO in air show very different affects on the PL spectra. PFO shows a dramatic increase in green emission (ca. 550 nm) after annealing in air for 60 minutes at 150° C. and the resulting green emission visibly dominates film color after only 20 minutes of thermal stressing.[45] In contrast, the PL spectra of PPTE and PMTE exhibit negligible change under identical conditions which severely degrade PFO response, as shown in FIG. 7. We attribute the increased stability to the stabilizing influence of the AE moieties at the 9-position in PPTE and PMTE.

Electroluminescence and Current-Voltage (I-V) Characteristics of PMTE II(b) Polymer Proof-of-concept polymer light-emitting diodes (PLEDs) with PMTE III(b) as the emitting layer were fabricated with the following sandwich structure: ITO/PEDOT-PSS/PMTE/Ca/Al. The electroluminescence spectrum acquired in ambient conditions did not shift over device testing time (ca. 30 min). PMTE exhibited turn-on voltages of ca. 4.5 V and exhibited blue electroluminescence as shown in FIG. 8.

Conclusions

The direct incorporation of AE functionality into PF materials at the 9-position has allowed for the preparation of thermally stable materials with excellent oxidative stability. Initial electroluminescence results support the use of this material system for PLED applications.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Full Citations for Documents Referred to in The Specification

1. Niu, Y. H.; Hou, Q.; Cao, Y. *Appl. Phys. Lett.* 2002, 81, 634-636.
2. Anni, M. *Appl. Phys. Lett.* 2008, 93, 023308.
3. Yap, B. K.; Xia, R.; Campoy-Quiles, M.; Stavrinou, P. N.; Bradley, D. D. C. *Nat. Mater.* 2008, 376-380.
4. Ryu, G.; Xia, R.; Bradley, D. D. C. *J. Phys.: Condens. Matter* 2007, 19, 056205.
5. Xia, R.; Heliotis, G.; Hou, Y.; Bradley, D. D. C. *Org. Electron.* 2003, 4, 165-177.
6. Heliotis, G.; Xia, R.; Bradley, D. D. C.; Turnbull, G. A.; Samuel, I. D. W.; Andrew, P.; Barnes, W. L. *Appl. Phys. Lett.* 2003, 83, 2118-2120.
7. Zhu, L.; Yang, C.; Zhang, W.; Qin, J. *Polymer* 2008, 49, 217-224.
8. Xing, C.; Shi, Z.; Yu, M.; Wang, S. *Polymer* 2008, 49, 2698-2703.
9. Yu, M.; He, F.; Tang, Y.; Wang, S.; Li, Y.; Zhu, D. *Macromol. Rapid Commun.* 2007, 28, 1333-1338.
10. Grigalevicius, S.; Forster, M.; Ellinger, S.; Landfester, K.; Scherf, U. *Macromol. Rapid Commun.* 2006, 27, 200-202.
11. Mondal, C. K.; Lee, J. Y. *J. Theor. Comput. Chem.* 2006, 5, 857-869.
12. Zhou, X. H.; Yan, J. C.; Pei, J. *Macromolecules* 2004, 37, 7078-7080.
13. Gulbinas, V.; Minevičiūtė, I.; Hertel, D.; Wellander, R.; Yartsev, A.; Sundström, V. *J. Chem. Phys.* 2007, 127, 144907.
14. Cho, S. Y.; Grimsdale, A. C.; Jones, D. J.; Watkins, S. E.; Holmes, A. B. *J. Am. Chem. Soc.* 2007, 129, 11910-11911.
15. Beljonne, D.; Pourtois, G.; Shuai, Z.; Hennebicq, E.; Scholes, G. D.; Brédas, J. L. *Synth. Met.* 2003, 137, 1369-1371.
16. Suh, H.; Jin, Y.; Park, S. H.; Kim, D.; Kim, J.; Kim, C.; Kim, J. Y.; Lee, K. *Macromolecules* 2005, 38, 6285-6289.

TABLE 1

Melting Temperature ($T_m$), Purity and Decomposition Temperature ($T_d$) under both $N_2$ and air of MTE and PTE monomers

| Monomer | $T_m$ (° C.)$^a$ | Purity$^b$ | $T_d$ (° C.) $N_2{}^c$ | $T_d$ (° C.) air$^d$ | $T_g{}^e$ (° C.) |
|---|---|---|---|---|---|
| MTE I(a) | 175 | 95.3 | 418 | 415 | 53 |
| PTE I(b) | 166 | 96.5 | 443 | 445 | 78 |

$^a T_m$ was determined with DSC at a heating rate of 0.5° C./min with 1-3 mg of sample.
$^b$Calorimetric purity determinations were made using 1-3 mg samples heated at 0.5° C./min with a DSC. The DSC purity determination software constructs a van't Hoff plot for the calculation of purity.
$^{c,d}$Onset decomposition temperatures (10% mass loss) were determined with a TGA in $N_2$ and air atmospheres, respectively.
$^e T_g$ was determined by heating at 10° C./min from 35° C. to 250° C. followed by cooling to −50° C. and heating again at 10° C./min to 250° C.

TABLE 2

Weight-Average Molecular Weight ($M_w$), Polydispersity Index (PDI), Glass Transition Temperature ($T_g$), Decomposition Temperature $T_d$, UV-vis Absorption Maxima ($\lambda_{abs,max}$), and Photoluminescence Maxima ($\lambda_{PL,max}$) of Polymers

| polymer | $M_w{}^a$ | PDI$^a$ | $T_g$ (° C.)$^b$ | $T_d$ (° C.)$^c$ | $\lambda_{abs,max}$ (nm)$^d$ solution | $\lambda_{abs,max}$ (nm)$^e$ film | $\lambda_{PL,max}$ (nm)$^d$ solution | $\lambda_{PL,max}$ (nm)$^e$ film |
|---|---|---|---|---|---|---|---|---|
| PMTE II(a) | 12000 | 1.8 | 98 | 515 (515)$^g$ | 376 | 390 | 420 | 430 |
| PPTE II(b) | 36000 | 3.9 | 184 | 534 (528)$^g$ | 374 | 387 | 420 | 440 |
| PFO$^f$ | 52000 | 2.2 | ~50 | 420 | 387 | 390 | 416 | 434 |

$^a M_w$ and PDI values were determined using GPC in THF with polystyrene standards.
$^b T_g$ (° C.) values were determined with DSC at a heating rate of 10° C./min after heating in vacuum at 100° C. for 24 hours.
$^c$Onset decomposition temperatures (10% mass loss) were determined with TGA in $N_2$.
$^d$Solution spectra were measured in toluene with a concentration of 0.001% w/v for $\lambda_{abs,max}$ and 0.00001 % w/v for $\lambda_{PL,max}$.
$^e$Films were drop-coated from toluene solution (1% w/v) and the first vibronic transition is displayed.
$^f$PFO was purchased from American Dye Source.
$^g$These values correspond to the second weight loss seen in FIG. 3 from the first TGA run.

17. Misaki, M.; Chikamatsu, M.; Yoshida, Y.; Azumi, R.; Tanigaki, N.; Yase, K.; Nagamatsu, S.; Ueda, Y. *Appl. Phys. Lett.* 2008, 93, 023304.

18. Becker, K.; Lupton, J. M.; Feldmann, J.; Nehls, B. S.; Galbrecht, F.; Gao, D.; Scherf, U. *Adv. Fund. Mater.* 2006, 16, 364-370.

19. Amara, J. P.; Swager, T. M. *Macromolecules* 2006, 39, 5753-5759.

20. Chan, K. L.; McKiernan, M. J.; Towns, C. R.; Holmes, A. B. *J. Am. Chem. Soc.* 2005, 127, 7662-7663.

21. Cho, H. J.; Jung, B. J.; Cho, N. S.; Lee, J.; Shim, H. K. *Macromolecules* 2003, 36, 6704-6710.

22. Chou, C. H.; Hsu, S. L.; Dinakaran, K.; Chiu, M. Y.; Wei, K. H. *Macromolecules* 2005, 38, 745-751.

23. Setayesh, S.; Grimsdale, A. C.; Weil, T.; Enkelmann, V.; Müllen, K.; Meghdadi, F.; List, E. J. W.; Leising, G. *J. Am. Chem. Soc.* 2001, 123, 946-953.

24. Marsitzky, D.; Vestberg, R.; Blainey, P.; Tang, B. T.; Hawker, C. J.; Carter, K. R. *J. Am. Chem. Soc.* 2001, 123, 6965-6972.

25. Cotter, R. J. *Engineering Plastics: A Handbook of Polyarylethers*; Gordan and Breach Science Publishers S.A.: Basel, 1995; p 357.

26. Mahoney, C. L.; Barnum, E. R.; Kerlin, W. W.; Sax, K. J.; Saari, W. S. *Journal of Chemical and Engineering Data* 1960, 5, 172-180.

27. Jiang, G.; Wu, J.; Yao, B.; Geng, Y.; Cheng, Y.; Xie, Z.; Wang, L.; Jing, X.; Wang, F. *Macromolecules* 2006, 39, 7950-7958.

28. Jiang, G.; Yao, B.; Geng, Y.; Cheng, Y.; Xie, Z.; Wang, L.; Jin, X.; Wang, F. *Macromolecules* 2006, 39, 1403-1409.

29. F. Ullmann. *Ber.* 1904, 37, 853.

30. Moroz, A. A.; Shvartsberg, M. S. *Russ. Chem. Rev.* 1974, 43, 679-689.

31. Lu, J.; Miyatake, K.; Hlil, A. R.; Hay, A. S. *Macromolecules* 2001, 34, 5860-5867.

32. Sirotkina, E. I.; Nesmeyanov, A. N.; Vol'kenau, N. A. *B. Acad. Sci. USSR CH+*. 1970, 18, 1413-1417.

37. Yamamoto, T.; Morita, A.; Miyazaki, Y.; Maruyama, T.; Wakayama, H.; Zhou, Z. H.; Nakamura, Y.; Kanbara, T.; Sasaki, S.; Kubota, K. *Macromolecules* 1992, 25, 1214-1223.

38. Ranger, M.; Leclerc, M. *Macromolecules* 1999, 32, 3306-3313.

39. Lindgren, L. J.; Wang, X.; Inganäs, O.; Andersson, M. R. *Synth. Met.* 2005, 154, 97-100.

40. Nadeau, N.; McFarlane, S.; McDonald, R.; Veinot, J. G. C. *Acta Cryst.* 2007, E63, O748-O749.

41. Khand, I. U.; Pauson, P. L.; Watts, W. E. *J. Chem. Soc. C.* 1968, 2261-2265.

42. Saragi, T. P. I.; Spehr, T.; Siebert, A.; Fuhrmann-Lieker, T.; Salbeck, J. *Chem. Rev.* 2007, 107, 1011-1065.

43. Grell, M.; Bradley, D. D. C.; Inbasekaran, M.; Woo, E. P. *Adv. Mater.* 1997, 9, 798-802.

44. Carter, K. R. *Macromolecules* 2002, 35, 6757-6759.

45. McFarlane, S.; Coumont, L. S.; Piercey, D. G.; McDonald, R.; Veinot, J. G. C. *Macromolecules,* 2008, In Press.

46. Schwartz, B. J. *Annu. Rev. Phy. Chem.* 2003, 54, 141-172.

The invention claimed is:

1. An aromatic ether-containing fluorene monomer of the Formula I:

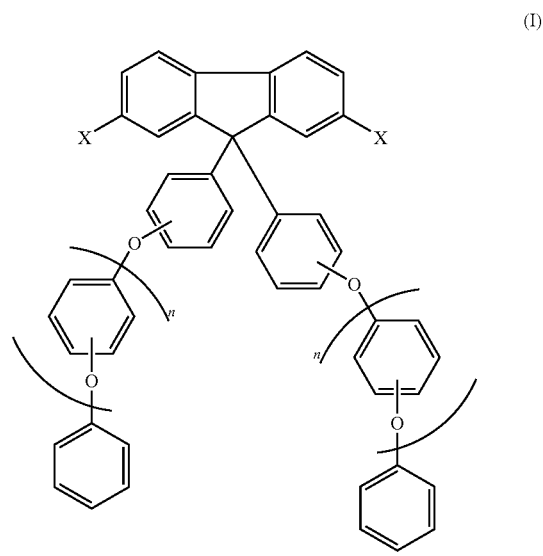

(I)

wherein X is a polymerization-enabling leaving group; and n is 0 or 1.

2. The monomer of claim 1, wherein X is bromo.

3. The monomer of claim 1, wherein n is 1.

4. The monomer of claim 1, wherein the aromatic ethers are attached at positions that are meta or para to each other.

5. The monomer of claim 1, having the following structure:

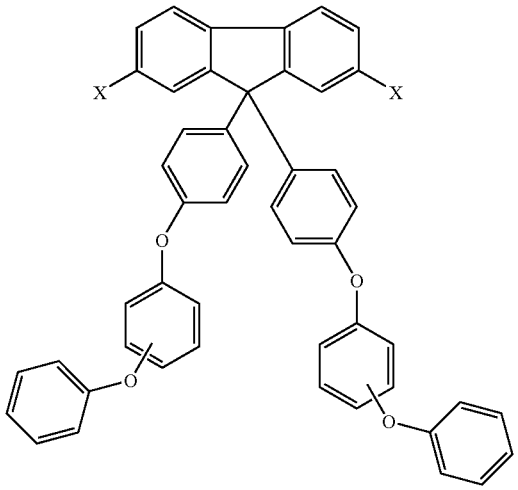

wherein X is a polymerization-enabling leaving group.

6. The monomer of claim 1, selected from:

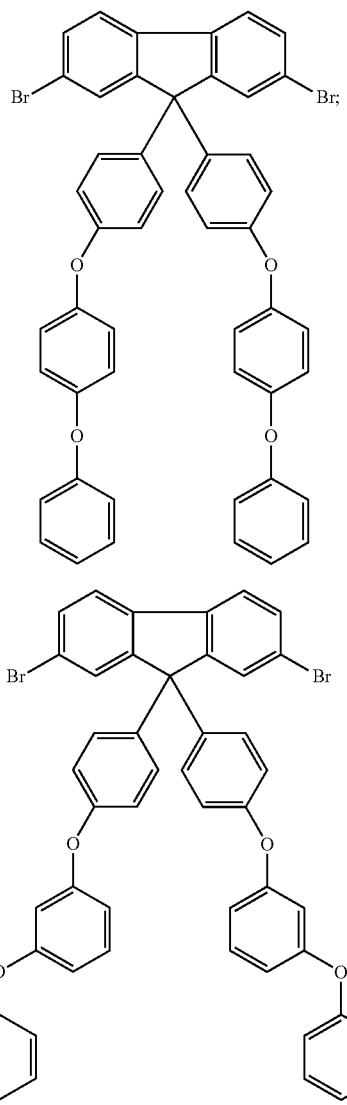

I(a)

I(b)

7. A process for the preparation of compounds of Formula I:

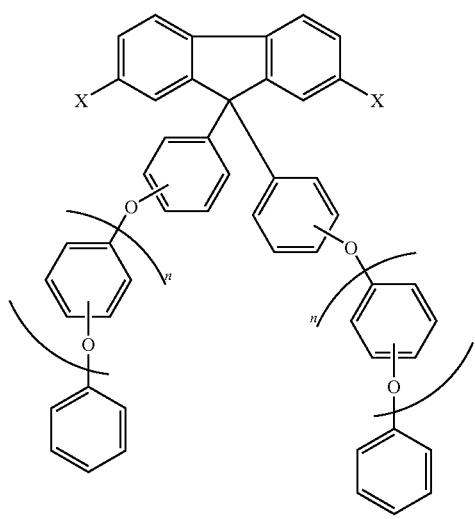

(I)

wherein X is a polymerization-enabling leaving group; and n is 0 or 1, comprising:

(a) reacting a compound of the Formula IV:

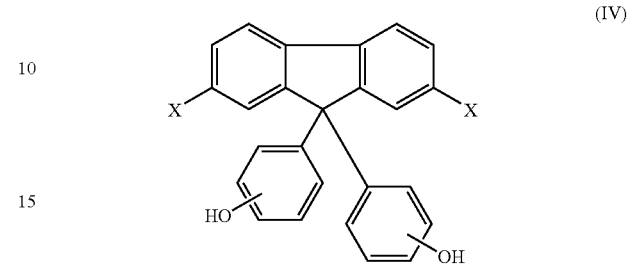

(IV)

wherein X is a polymerization-enabling leaving group, with a compound of the Formula V:

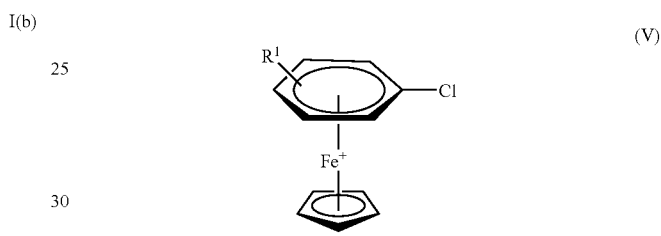

(V)

wherein $R^1$=H for compounds of Formula I wherein n is 0 and $R^1$=Cl for compounds of Formula I wherein n is 1, under conditions to form a compound of the Formula VI

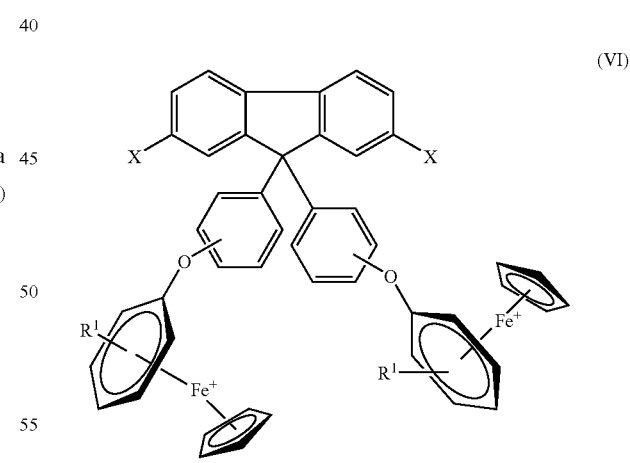

(VI)

wherein X is a polymerization-enabling leaving group and $R^1$ is H for compounds of Formula I wherein n is 0 and $R^1$ is Cl for compounds of Formula I wherein n is 1;

(b) when $R^1$ is H, reacting the compounds of Formula VI under conditions to remove the $CpFe^+$ group to form a compound of Formula I wherein n is 0; or when $R^1$ is Cl, reacting the compounds of the Formula VI with a compound of the Formula VII:

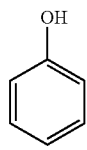
(VII)

under conditions to form a compound of the Formula VIII:

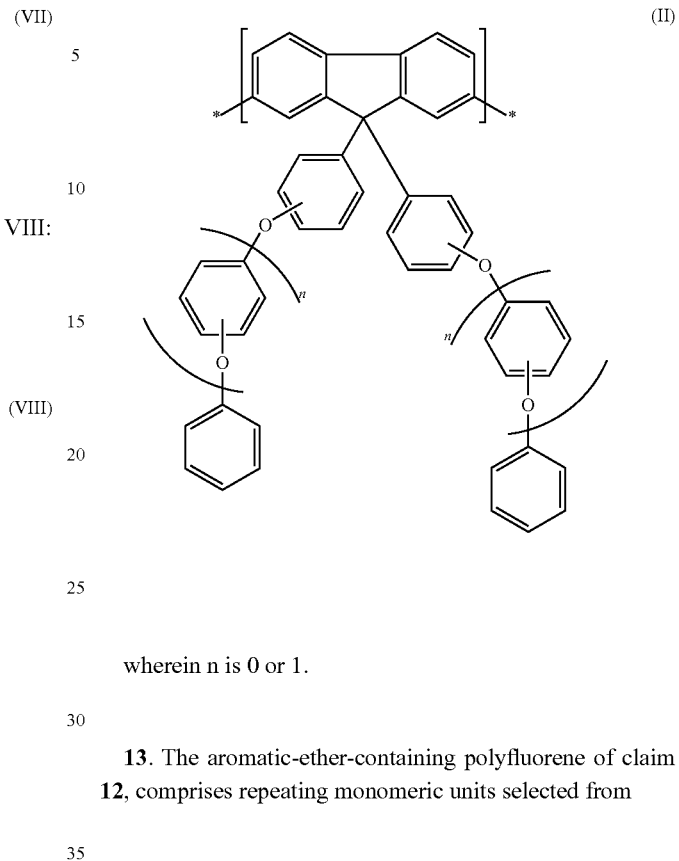
(VIII)

(II)

wherein n is 0 or 1.

13. The aromatic-ether-containing polyfluorene of claim 12, comprises repeating monomeric units selected from wherein $R^2$ is O-Ph; and (c) treating the compounds of the Formula VIII under conditions to remove the CpFe$^+$group to form a compound of Formula I wherein n is 1.

8. The process of claim 7, wherein the conditions to form a compound of the Formula VI comprise reacting the compounds of Formula IV and V in the presence of a base in an inert solvent at room temperature for about 12 hours to about 36 hours.

9. The process of claim 7, wherein the conditions to remove the CpFe$^+$group comprise reacting the compound of Formula VI or VIII in a suitable high boiling solvent and heating in a microwave reactor, to a temperature of about 150° C. to about 250° C., for about 10 to about 15 minutes.

10. The process of claim 7, wherein the conditions to form a compound of the Formula VIII comprise reacting the compounds of the Formula VI and VII presence of a base in an inert solvent at room temperature for about 48 to about 96 hours.

11. The process of claim 7, wherein in the preparation of the compounds of the Formula VIII, the compounds of the Formula VI, wherein $R^1$ is Cl are not isolated.

12. An aromatic-ether-containing polyfluorene comprising repeating monomeric units of the Formula II:

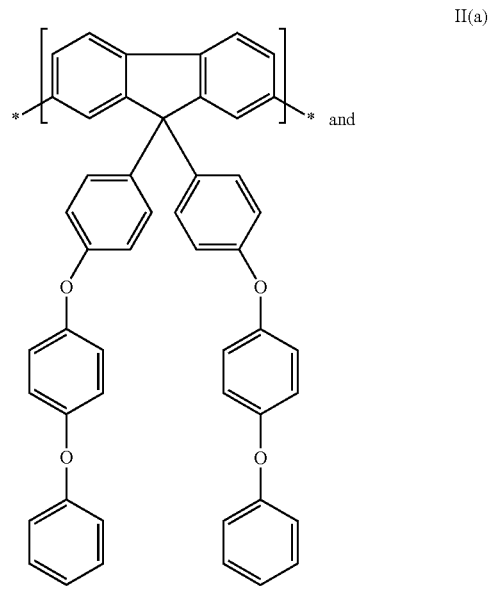
II(a)

and

-continued

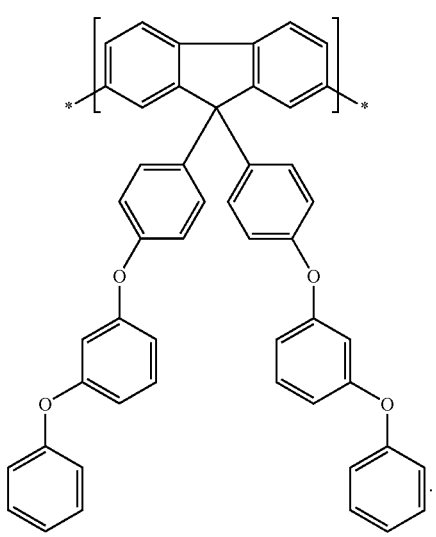

II(b)

14. An aromatic-ether-containing polyfluorene of the Formula III:

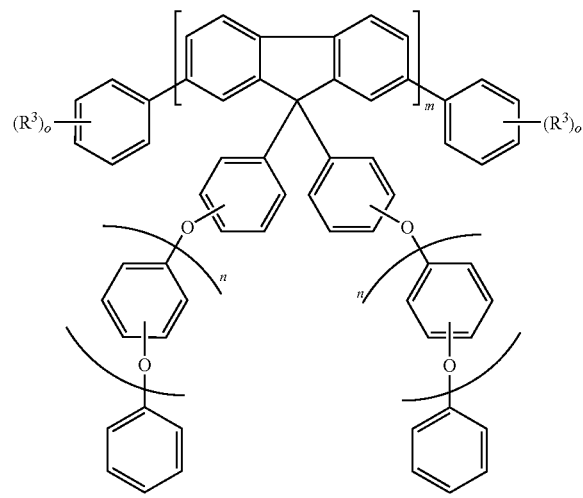

(III)

wherein $R^3$ is $C_{1-6}$alkyl;
m is an integer from 1 to 10,000;
n is 0 or 1; and
o is 0, 1, 2, 3, 4 or 5.

15. The aromatic-ether-containing polyfluorene of claim 14, wherein n is 1.

16. The aromatic-ether-containing polyfluorene of claim 14, wherein $R^3$ is methyl and o is 2.

17. The aromatic-ether-containing polyfluorene of claim 16, wherein the 2 $R^3$ groups are located at the 3 and 5 positions of the phenyl ring.

18. The aromatic-ether-containing polyfluorene of claim 14 selected from:

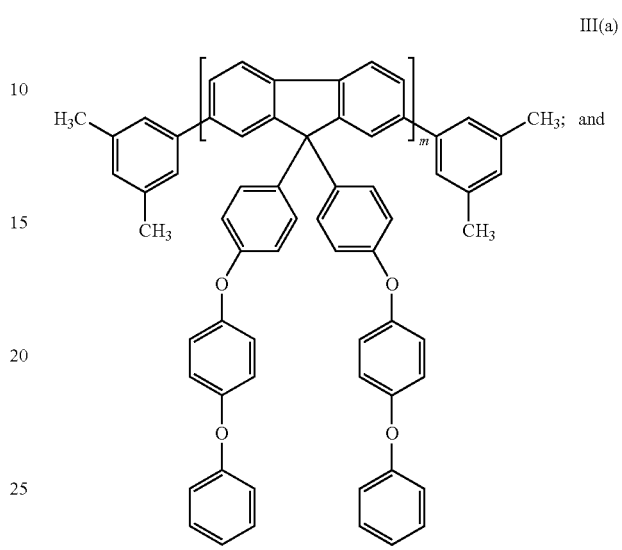

III(a)

and

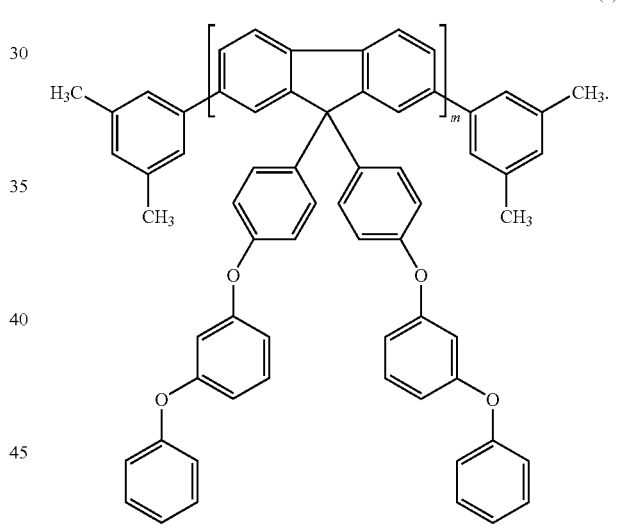

III(b)

19. A light-emitting solid state device comprising an aromatic-ether-containing polyfluorene comprising repeating monomeric units of the Formula II of claim 12.

20. The light-emitting solid state device according to claim 19, configured as a light-emitting diode or a light-emitting electrochemical cell.

* * * * *